US00RE45534E

(19) United States
(12) Reissued Patent
Huennekens et al.

(10) Patent Number: US RE45,534 E
(45) Date of Reissued Patent: Jun. 2, 2015

(54) VASCULAR IMAGE CO-REGISTRATION

(71) Applicant: Volcano Corporation, San Diego, CA (US)

(72) Inventors: Richard Scott Huennekens, San Diego, CA (US); Stephen M. Fry, El Dorado Hills, CA (US); Blair D. Walker, Mission Viejo, CA (US); Jon D. Klingensmith, El Dorado Hills, CA (US); Nancy Perry Pool, El Dorado Hills, CA (US); Vincent J. Burgess, San Diego, CA (US); William R. Kanz, Sacramento, CA (US)

(73) Assignee: Volcano Corporation, San Diego, CA (US)

(21) Appl. No.: 13/865,803

(22) Filed: Apr. 18, 2013

Related U.S. Patent Documents

Reissue of:
(64) Patent No.: 7,930,014
Issued: Apr. 19, 2011
Appl. No.: 11/329,609
Filed: Jan. 11, 2006

U.S. Applications:
(60) Provisional application No. 60/694,014, filed on Jun. 24, 2005, provisional application No. 60/642,893, filed on Jan. 11, 2005.

(51) Int. Cl.
*A61B 5/05* (2006.01)
*A61B 5/06* (2006.01)
*A61B 19/00* (2006.01)

(52) U.S. Cl.
CPC ..... *A61B 5/06* (2013.01); *A61B 19/5244* (2013.01)

(58) Field of Classification Search
USPC ..... 600/407, 424, 425–427, 437, 453–455, 600/462, 466, 467, 473, 476; 382/159, 165, 382/170, 181
See application file for complete search history.

(56) References Cited

U.S. PATENT DOCUMENTS 4,173,228 A 11/1979 Van Steenwyk
4,821,731 A 4/1989 Martinelli
(Continued)

FOREIGN PATENT DOCUMENTS

CA 2 449 080 5/2005
JP HEI 5-084248 4/1993
(Continued)

OTHER PUBLICATIONS

Translated Japanese Office Action dated May 2, 2014 in reference to Japanese Application No. 2013-015279, 3 pages.
(Continued)

*Primary Examiner* — James Kish
(74) *Attorney, Agent, or Firm* — Haynes and Boone, LLP

(57) ABSTRACT

A system and method for providing a vascular image are disclosed wherein a single composite display simultaneously provides a first view of a patient including an angiogram image and a second view including an intravascular image rendered from information provided by an imaging probe mounted on a distal end of a flexible elongate member. A cursor, having a position derived from image information provided by a radiopaque marker proximate the imaging probe, is displayed within the angiogram image to correlate the position of the imaging probe to a presently displayed intravascular image and thus provide an easily discernable identification of a position within a patient corresponding to a currently displayed intravascular image. The resulting composite display simultaneously provides: an intravascular image that includes information about a vessel that is not available from an angiogram and a current location within a vessel of a source of intravascular image data from which the intravascular image is rendered.

99 Claims, 9 Drawing Sheets

(56) References Cited

U.S. PATENT DOCUMENTS

| | | | | |
|---|---|---|---|---|
| 4,838,879 | A | 6/1989 | Tanabe | |
| 4,875,165 | A | 10/1989 | Fencil | |
| 4,938,220 | A | 7/1990 | Mueller, Jr. | |
| 5,042,486 | A | 8/1991 | Pfeiler | |
| 5,109,859 | A | 5/1992 | Jenkins | |
| 5,159,931 | A | 11/1992 | Pini | |
| 5,203,777 | A | 4/1993 | Lee | |
| 5,207,226 | A * | 5/1993 | Bailin et al. | 600/454 |
| 5,357,550 | A * | 10/1994 | Asahina et al. | 378/98.5 |
| 5,386,828 | A | 2/1995 | Owens | |
| 5,429,617 | A | 7/1995 | Hammersmark | |
| 5,485,840 | A | 1/1996 | Bauman | |
| 5,540,229 | A | 7/1996 | Collet-Billon | |
| 5,592,939 | A | 1/1997 | Martinelli | |
| 5,690,113 | A | 11/1997 | Sliwa, Jr. | |
| 5,699,446 | A | 12/1997 | Rougee | |
| 5,699,805 | A * | 12/1997 | Seward et al. | 600/459 |
| 5,709,206 | A | 1/1998 | Teboul | |
| 5,729,129 | A | 3/1998 | Acker | |
| 5,744,953 | A | 4/1998 | Hansen | |
| 5,752,513 | A | 5/1998 | Acker | |
| 5,771,895 | A | 6/1998 | Slager | |
| 5,824,042 | A | 10/1998 | Lombardi | |
| 5,830,145 | A | 11/1998 | Tenhoff | |
| 5,840,025 | A | 11/1998 | Ben-Haim | |
| 5,872,861 | A | 2/1999 | Makram-Ebeid | |
| 5,876,344 | A | 3/1999 | Baker et al. | |
| 5,899,860 | A | 5/1999 | Pfeiffer | |
| 5,921,978 | A | 7/1999 | Thompson | |
| 5,954,647 | A | 9/1999 | Bova | |
| 5,957,844 | A | 9/1999 | Dekel | |
| 5,993,390 | A | 11/1999 | Savord | |
| 6,014,473 | A | 1/2000 | Hossack | |
| 6,016,439 | A | 1/2000 | Acker | |
| 6,024,763 | A | 2/2000 | Lenker | |
| 6,035,226 | A | 3/2000 | Panescu | |
| 6,036,682 | A | 3/2000 | Lange | |
| 6,083,167 | A | 7/2000 | Fox | |
| 6,095,976 | A | 8/2000 | Nachtomy | |
| 6,102,865 | A | 8/2000 | Hossack | |
| 6,104,944 | A | 8/2000 | Martinelli | |
| 6,132,376 | A | 10/2000 | Hossack | |
| 6,148,095 | A * | 11/2000 | Prause et al. | 382/131 |
| 6,152,878 | A | 11/2000 | Nachtomy | |
| 6,159,225 | A | 12/2000 | Makower | |
| 6,166,740 | A | 12/2000 | Malzbender | |
| 6,190,353 | B1 | 2/2001 | Makower | |
| 6,201,900 | B1 | 3/2001 | Hossack | |
| 6,216,029 | B1 | 4/2001 | Paltieli | |
| 6,233,476 | B1 | 5/2001 | Strommer | |
| 6,246,898 | B1 | 6/2001 | Vesely | |
| 6,248,075 | B1 | 6/2001 | McGee | |
| 6,273,858 | B1 * | 8/2001 | Fox et al. | 600/466 |
| 6,275,724 | B1 | 8/2001 | Dickinson | |
| 6,285,903 | B1 | 9/2001 | Rosenthal | |
| 6,298,261 | B1 | 10/2001 | Rex | |
| 6,314,310 | B1 | 11/2001 | Ben-Haim | |
| 6,351,513 | B1 | 2/2002 | Bani-Hashemi | |
| 6,360,027 | B1 | 3/2002 | Hossack | |
| 6,374,134 | B1 | 4/2002 | Bladen | |
| 6,389,104 | B1 | 5/2002 | Bani-Hashemi | |
| 6,405,072 | B1 | 6/2002 | Cosman | |
| 6,464,645 | B1 * | 10/2002 | Park et al. | 600/462 |
| 6,501,848 | B1 | 12/2002 | Carroll | |
| 6,515,657 | B1 | 2/2003 | Zanelli | |
| 6,546,271 | B1 | 4/2003 | Reisfeld | |
| 6,574,498 | B1 | 6/2003 | Gilboa | |
| 6,577,889 | B2 | 6/2003 | Ichihashi | |
| 6,612,992 | B1 | 9/2003 | Hossack | |
| 6,638,222 | B2 | 10/2003 | Chandrasekaran et al. | |
| 6,650,927 | B1 | 11/2003 | Keidar | |
| 6,673,018 | B2 | 1/2004 | Friedman | |
| 6,718,054 | B1 | 4/2004 | Lorigo | |
| 6,719,700 | B1 | 4/2004 | Willis | |
| 6,775,404 | B1 | 8/2004 | Pagoulatos | |
| 6,785,571 | B2 | 8/2004 | Glossap | |
| 6,805,132 | B2 | 10/2004 | Willis | |
| 6,831,644 | B2 | 12/2004 | Lienard | |
| 6,895,267 | B2 | 5/2005 | Panescu | |
| 6,896,657 | B2 | 5/2005 | Willis | |
| 6,923,768 | B2 | 8/2005 | Camus | |
| 6,970,733 | B2 | 11/2005 | Willis | |
| 6,970,734 | B2 | 11/2005 | Eidenschink | |
| 7,052,463 | B2 * | 5/2006 | Peszynski et al. | 600/459 |
| 2001/0041842 | A1 | 11/2001 | Eberle et al. | |
| 2002/0019644 | A1 | 2/2002 | Hastings | |
| 2002/0049375 | A1 | 4/2002 | Strommer | |
| 2002/0099428 | A1 | 7/2002 | Kaufman | |
| 2002/0115931 | A1 * | 8/2002 | Strauss et al. | 600/420 |
| 2003/0220555 | A1 | 11/2003 | Heigl | |
| 2003/0231789 | A1 | 12/2003 | Willis | |
| 2004/0114146 | A1 | 6/2004 | Willis | |
| 2004/0138548 | A1 | 7/2004 | Strommer | |
| 2004/0254463 | A1 * | 12/2004 | Lehman | 600/437 |
| 2005/0096647 | A1 | 5/2005 | Steinke | |
| 2005/0113685 | A1 | 5/2005 | Maschke | |
| 2005/0203369 | A1 | 9/2005 | Sathyanarayana | |
| 2006/0036167 | A1 * | 2/2006 | Shina | 600/433 |

FOREIGN PATENT DOCUMENTS

| | | |
|---|---|---|
| JP | HEI 10-137238 | 5/1998 |
| WO | WO 2004/075756 A1 | 9/2004 |

OTHER PUBLICATIONS

Dorland's Medical Dictionary, www.mercksource.com/pp/us/cns/cns_hl_dorlands_split.jsp?pg=/ppdocs/us/common/dorlands/dorland/one/000005102.htm.*

The On-line Medical Dictionary, http://cancerweb.ncl.ac.uk/cgi-bin/omd?angiogram.*

MedTerms.com, http://www.medterms.com/script/main/art.asp?articlekey=2256.*

Dictionary of Cancer Terms, http://www.cancer.gov/Templates/db_alpha.aspx?CdrID=46530.*

Medical Dictionary, The Free Dictionary; http://medical-dictionary.thefreedictionary.com/angiogram.*

International Search Report for PCT/US06/00942 dated Sep. 20, 2007.

Written Opinion of the International Searching authority for PCT/US06/00942 dated Sep. 20, 2007.

No author, "Radiation Safety Manual for the Fluoroscopist," Internet source, 2000, Saint Luke's Hospital of Kansas City, Kansas City, U.S.A.

Cavaye, D., Tabbara, M., Kopchok, G., Laas, T., White, R., "Three Dimensional Vascular Ultrasound Imaging", The American Surgeon, 1991, pp. 751-755, vol. 57, No. 12, Lippincott, Philadelphia, U.S.A.

Chen, S., Metz, C., "Improved Determination of Biplane Imaging Geometry from Two Projection Images and Its Application to Three-Dimensional Reconstruction of Coronary Trees", Medical Physics, 1997, pp. 633-654, vol. 24, No. 5, American Institute of Physics, New York, U.S.A.

Chen, S., Carroll, J., "3-D Reconstruction of Coronary Arterial Tree to Optimize Angiographic Visualization", IEEE Transactions on Medical Imaging, 2000, pp. 318-336, vol. 19, No. 4, Institute of Electrical and Electronics Engineers, New York, U.S.A.

Chen, S., Carroll, J., Messenger, J., "Quantitative Analysis of Reconstructed 3-D Coronary Arterial Tree and Intracoronary Devices", IEEE Transactions on Medical Imaging, 2002, pp. 724-740, vol. 21, No. 7, Institute of Electrical and Electronics Engineers, New York, U.S.A.

Cothren, R., Shekhar, R., Tuzcu, E., Nissen, S., Cornhill, J., Vince, D., "Three-Dimensional Reconstruction of the Coronary Artery Wall by Image Fusion of Intravascular ultrasound and Bi-Plane Angiography", International Journal of Cardiac Imaging, 2000, pp. 69-85, vol. 16, No. 2, Nijhoff, Boston, U.S.A.

Evans, J., Ng, K., Wiet, S., Vonesh, M., Burns, W., Radvany, M., Kane, B., Davidson, D., Roth, S., Kramer, B., Meyers, S., McPherson, D., "Accurate Three-Dimensional Reconstruction of

(56) References Cited

OTHER PUBLICATIONS

Intravascular Ultrasound Data", Circulation, 1996, pp. 567-576, vol. 93, No. 3, American Hearth Association, Dallas, U.S.A.
Falk, V., Mourgues, F., Adhami, L., Jacobs, S., Thiele, H., Nitzsche, S., Mohr, F., Coste-Maniere, E., "Cardio Navigation: Planning, Simulation, and Augmented Reality in Robotic Assisted Endoscopic Bypass Grafting", The Annals of Thoracic Surgery, 2005, pp. 2040-2048, vol. 79, No. 6, Little, Brown & Co., Boston, U.S.A.
Fencil, L., Doi, K., Hoffman, K., "Accurate Analysis of Blood Vessel Sizes and Stenotic Lesions Using Stereoscopic DSA System", Investigative Radiology, 1988, pp. 33-41, vol. 23, No. 1, Lippincott, Philadelphia, U.S.A.
Fujita, H., Doi, K., Fencil, L., Chua, K., "Image Feature Analysis and Computer-Aided Diagnosis in Digital Radiography. 2. Computerized Determination of Vessel Sizes in Digital Subtraction Angiography", Medical Physics, 1987, pp. 549-556, vol. 14, No. 4, American Institute of Physics, New York, U.S.A.
Godbout, B., De Guise, J., Soulez, G., Cloutier, G., "3D Elastic Registration of Vessel Structures from IVUS data on Biplane Angiography", Academic Radiology, 2005, pp. 10-16, vol. 12, No. 1, Association of University Radiologists, Reston, U.S.A.
Guggenheim, N., Doriot, P., Dorsaz, P., Descouts, P., Rutishauser, W., "Spatial Reconstruction of Coronary Arteries from Angiographic Images", Physics in Medicine and Biology, 1991, pp. 99-110, vol. 36, No. 1, Institute of Physics, London, England.
Hoffmann, K., Sen, A., Lan, L., Chua, K., Esthappan, J., Mazzucco, M., "A System for Determination of 3D Vessel Tree Centerlines from Biplane Images", The International Journal of Cardiac Imaging, 2000, pp. 315-330, vol. 16, No. 5, Nihoff, Boston, U.S.A.
Jiang, H., Chen, W., Wang, G., Liu, H., "Localization Error Analysis for Stereo X-ray Image Guidance with Probability Method", Medical Engineering & Physics, 2001, pp. 573-581, vol. 23, No. 8, Butterworth-Heinemann, Oxford, England.
Leggett, M., Leotta, D., Bolson, E., McDonald, J., Martin, R., Li, X., Otto, C., Sheehan, F., "System for Quantitative Three-Dimensional Echocardiography of the Left Ventricle Based on a Magnetic-Field Position and Orientation Sensing System", IEEE Transactions on Biomedical Engineering, 1998, pp. 494-504, vol. 45, No. 4, Institute of Electrical and Electronics Engineers, New York, U.S.A.
Leotta, D., "An Efficient Calibration Method for Freehand 3-D Ultrasound Imaging Systems", Ultrasound in Medicine & Biology, 2004, pp. 999-1008, vol. 30, No. 7, Elsevier, New York, U.S.A.
Liu, I., Sun, Y., "Fully Automatic Reconstruction of Three-Dimensional Vascular Tree Structures from Two Orthogonal Views Using Computational Algorithms and Production Rules", Optical Engineering, 1992, pp. 2197-2207, vol. 31, No. 10, The Society of Photooptical Instrumentation Engineers, Redondo Beach, U.S.A.
Meyer, S., Wolf, P., "Registration of Three-Dimensional Cardiac Catheter Models to Single-Plane Fluoroscopic Images", IEEE Transactions on Biomedical Engineering, 1999, pp. 1471-1479, vol. 46, No. 12, Institute of Electrical and Electronics Engineers, New York, U.S.A.
Movassaghi, B., Grass, V., Viergever, M., Niessen, W., "A Quantitative Analysis of 3-D Coronary Modeling from Two or More Projection Images", IEEE Transactions on Medical Imaging, 2004, pp. 1517-1531, vol. 23, No. 12, Institute of Electrical and Electronics Engineers, New York, U.S.A.
Prause, G., DeJong, S., McKay, C., Sonka, M., "Accurate 3-D Reconstruction of Tortuous Coronary Vessels Using Biplane Angiography and Intravascular Ultrasound" *in SPIE Medical imaging 1997. Physiology and function from multidimensional images :* Feb. 23-25, 1997, Newport Beach, California, 1997, pp. 225-234, vol. 3033, Ed.Hofman, E., SPIE, Bellingham, U.S.A.
Prause, G., DeJong, S., McKay, C., Sonka, M., "Semi-Automated Segmentation and 3-D Reconstruction of Coronary Trees: Biplane Angiography and Intravascular Ultrasound Data Fusion" in *SPIE Medical imaging 1996. Physiology and function from multidimensional images :* Feb. 11-13, 1996, Newport Beach, California, 1996, pp. 82-92, vol. 2709, Ed.Hofman, E., SPIE, Bellingham, U.S.A.
Rotger, D., Radeva, P., Mauri, J., Fernandez-Nofrerias, E., "Internal and External Coronary Vessel Images Registration"in *Topics in Artificial Intelligence,* 2002, pp. 408-418, Eds. Escrig Monferrer M. and Toledo Lobo, F., Springer-Verlag, Berlin, Germany.
Sheehan, H., Hodgson, J., "Intravascular Ultrasound: Advantages and Indications," International Journal of Cardiac Imaging, 1995, pp. 9-14, vol. 11, No. Suppl 1, Kluwer Academic Publishers, Boston, U.S.A.
Sherknies, D., Meunier, J., Mongrain, R., Tardif, J., "Three-Dimensional Trajectory Assessment of an IVUS Transducer from Single-Plane Cineangiograms: A Phantom Study", IEEE Transactions on Biomedical Engineering, 2005, pp. 543-548, vol. 52, No. 3, Institute of Electrical and Electronics Engineers, New York, U.S.A.
Takemura, A., Harauchi, H., Suzuki, M., Hoffmann, K., Inamura, K., Umeda, T., "An Algorithm for Mapping the Catheter Tip Position on a Fluorograph to the Three-Dimensional Position in Magnetic Resonance Angiography Volume Data", Physics in Medicine and Biology, 2003, pp. 2697-2711, vol. 48, No. 16, Institute of Physics, London, England.
Van Walsum, T., Baert, S., Niessen, W., "Guide Wire Reconstruction and Visualization in 3DRA Using Monoplane Fluoroscopic Imaging", IEEE Transactions on Medical Imaging, 2005, pp. 612-623, vol. 24, No. 5, Institute of Electrical and Electronics Engineers, New York, U.S.A.
Wahle, A., Prause, G., Von Birgelen, C., Erbel, R., Sonka, M., "Automated Calculation of the Axial Orientation of Intravascular Ultrasound Images by Fusion with Biiplane Angiography" in *SPIE Medical imaging 1999. Image processing :* Feb. 22-25, 1999, San Diego, California, 1999, pp. 1094-1104, vol. 3661, Ed. Hanson, K., SPIE, Bellingham, U.S.A.
Wahle, A., Mitchell, S., Ramaswamy, S., Chandran, K., Sonka, M., "Four-Dimensional Coronary Morphology and Computational Hemodynamics" in *SPIE Medical imaging 2001 : Image processing :* Feb. 19-22, 2001, San Diego, USA, 2001, pp. 743-754, vol. 4322, Eds. Sonka, M. and Hanson, K., SPIE, Bellingham, U.S.A.
Wahle, A., Lopez, J., Pennington, E., Meeks, S., Braddy, K., Fox, J., Brennan, T., Buiatti, J., Rossen, J., Sonka, M., "Effects of Vessel Geometry and Catheter Position on Dose Delivery in Intracoronary Brachytherapy", IEEE Transactions on Biomedical Engineering, 2003, pp. 1286-1295, vol. 50, No. 11, Institute of Electrical and Electronics Engineers, New York, U.S.A.
Wahle, A., Olszewski, M., Sonka, M., "Interactive Virtual Endoscopy in Coronary Arteries Based on Multimidality Fusion", IEEE Transactions on Medical Imaging, 2004, pp. 1391-1403, vol. 23, No. 11, Institute of Electrical and Electronics Engineers, New York, U.S.A.
Weichert, F., Wawro, M., Muller, H., Wilke, C., "Registration of Biplane Angiography and Intravascular Ultrasound for 3D Vessel Reconstruction", Methods of Information in Medicine, 2004, pp. 398-402, vol. 43, No. 4, F.K. Schattauer, Stuttgart, Germany.
Weichert, F., Wawro, M., Wilke, C., "A 3D Computer Graphics Approach to Brachytherapy Planning", The International Journal of Cardiovascular Imaging, 2004, pp. 173-182, vol. 20, No. 3, Kluwer Academic Publishers, Boston, U.S.A.

* cited by examiner

VASCULAR IMAGE CO-REGISTRATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application claims priority of Huennekens et al. U.S. provisional application Ser. No. 60/642,893 filed on Jan. 11, 2005, entitled "Catheter Image Co- Registration," and Walker et al. U.S. provisional application Ser. No. 60/694,014 filed on Jun. 24, 2005, entitled "Three-Dimensional Co-Registration For Intravascular Diagnosis and Therapy", the contents of both of the above-identified provisional applications are expressly incorporated herein by reference in their entirety including the contents and teachings of any references contained therein.

AREA OF THE INVENTION

The present invention generally relates to imaging blood vessels. More particularly, the present invention is directed to methods and systems for generating composite displays relating a first image rendered from a first type of data and a second image rendered from a second type of data. A particular example of such composite display comprises an angiogram displayed along-side an IVUS image.

BACKGROUND OF THE INVENTION

In coronary arteries, vascular diseases including vessel lumen narrowing, usually due to atherosclerotic plaque, can lead to reduced blood flow to a heart muscle, angina (chest pain) and myocardial infarction—a heart attack. A variety of interventional treatments of cardiovascular disease are presently available to identify and treat such narrowing of a vessel lumen. Examples of such treatments include balloon angioplasty and/or deployment of stents. Diagnostic imaging is utilized to identify the extent and/or type of blockages within vessels prior to and/or during the treatment of such blockages. Diagnostic imaging enables doctors to ensure proper treatment of diseased vessels and verify the efficacy of such treatment.

In general, two distinct manners exist for generating diagnostic images for the identification and treatment of cardiovascular disease within a vasculature. A first manner of diagnostic imaging involves generating a radiological image of a stream flowing through a blood vessel's lumen from outside the vessel lumen. The purpose of generating an image of such flow is to identify blockages within diseased blood vessels that restrict blood flow. The extent of a vessel's lumen is traditionally imaged using angiography, which involves rendering a two-dimensional view of one or more vessels within a portion of a patient's vasculature through which radiopaque contrast media has been injected. The two-dimensional angiographic image can also be viewed real time by fluoroscopy. During such procedures, the images are potentially captured in various digital media, or in cine angiography (cine). Cine angiography, though rendering higher quality images of blood vessel lumens, exposes patients to high levels of ionizing radiation.

Fluoroscopy, generally using substantially less intense radiation than angiography, is used by physicians primarily to visually guide diagnostic and therapeutic catheters or guidewires, including one or more radiopaque markers, through vessels. The radiation intensity during fluoroscopy is typically one-tenth the intensity of radiation to which a patient is exposed during cine angiography. Many catheters have radiopaque markers that are viewable on a fluoroscope, thereby enabling a physician to track the location/path of such catheters as they are inserted within and/or withdrawn from patients. The platinum spring coil of guidewires also serves as a radiopaque marker. The lower radiation intensity of fluoroscopy allows a greater duration of use during a diagnostic/treatment procedure. However, due to its greater time of use, the total radiation exposure from fluoroscopy during an interventional treatment procedure can greatly exceed the radiation exposure during a typical cine angiography procedure. Thus, it is incumbent upon a physician to minimize the duration of time that a fluoroscope is used during a diagnostic and/or interventional treatment procedure.

The first manner of imaging, described above, has a number of drawbacks. For example, limited flow of contrast media near vessel walls and extreme variations in vessel cross-sections can result in incomplete filling of the vessel with a sufficient concentration of contrast media. As a consequence, the diameters of vessel segments can be misrepresented in an angiographic image. For example, a left main coronary artery cross-section is often underestimated by angiography. This can be problematic when attempting to judge the significance of a blockage within the vessel or when choosing the size of the treatment balloon or stent. An under-sized balloon or stent will not provide as effective treatment as a properly sized device. Furthermore, in angiography, a vessel's cross-section is determined by a two-dimensional view which may not accurately represent an actual extent of blood vessel narrowing.

Furthermore, to achieve an optimum treatment result, it is important to correctly determine a true target diameter of a native blood vessel—the diameter of a non-diseased blood vessel. However, angiography is ineffective in determining the target diameter of a vessel with disease along its entire length. For example, since vessels tend to taper in diameter along their length, a uniformly narrowed vessel may appear normal in an angiographic image.

Finally, angiography does not facilitate differentiating between different types of tissue found in atherosclerotic plaque. For example, in coronary arteries prone to producing a heart attack, necrotic tissue is thought to be more prevalent than purely fibrous tissue. Thus, while providing a good way to identify severe blockages, angiography is not always the best diagnostic imaging tool due to the incomplete nature of the angiographic image data.

The second manner of intravascular imaging comprises imaging the vessel itself using a catheter-mounted intravascular probe. Intravascular imaging of blood vessels provides a variety of information about the vessel including: the cross-section of the lumen, the thickness of deposits on a vessel wall, the diameter of the non-diseased portion of a vessel, the length of diseased sections, and the makeup of the atherosclerotic plaque on the wall of the vessel.

Several types of catheter systems have been designed to track through a vasculature to image atherosclerotic plaque deposits on vessel walls. These advanced imaging modalities include, but are not limited to, intravascular ultrasound (IVUS) catheters, magnetic resonance imaging (MRI) catheters and optical coherence tomography (OCT) catheters. In addition, thermography catheters and palpography catheters have also been demonstrated to generate vessel image data via intravascular probes. Other catheter modalities that have been proposed include infrared or near-infrared imaging.

In operation, these intravascular catheter-mounted probes are moved along a vessel in the region where imaging is desired. As the probe passes through an area of interest, sets of image data are obtained that, correspond to a series of "slices" or cross-sections of the vessel, the lumen, and surrounding tissue. As noted above, the catheters include radiopaque markers. Such markers are generally positioned near a distal catheter tip. Therefore, the approximate location of the imaging probe can be discerned by observing the catheterization procedure on either a fluoroscope or angiographic image. Typically imaging catheters are connected to a dedicated console, including specialized signal processing hardware and software, and display. The raw image data is received by the console, processed to render an image including features of concern, and rendered on the dedicated display device.

For example, IVUS images used to diagnose/treat vascular disease generally comprise sets of cross-sectional image "slices" of a vessel. A grayscale cross-sectional slice image is rendered, at each of a set of positions along the vessel based upon the intensity of ultrasound echoes received by an imaging probe. Calcium or stent struts, which produce relatively strong echoes, are seen as a lighter shade of gray. Blood or vessel laminae, which produce weaker echoes, are seen as a darker shade of gray.

Atherosclerotic tissue is identified as being the portion of a cross-sectional image between an internal elastic lamina (IEL) and an external elastic lamina (EEL). The ability to see the vessel lumen, and calculate its dimensions, allows the diameters and cross-sectional area of the vessel to be determined more reliably than the limited two-dimensional angiography. Because IVUS does not rely upon dispersing a contrast agent, IVUS is especially useful in generating images of the left main coronary artery as described above. Furthermore, the ability to view the EEL, and calculate its dimensions, allows an IVUS image to render a more reliable determination than angiography, of the correct diameter and length of the balloon or stent to use when restoring proper blood flow to a blocked/diseased vessel. Advanced IVUS images have also been described which perform tissue characterization and denote different types of tissue with a color code. One such modality is described in Vince, U.S. Pat. No. 6,200,268. Like IVUS, the other catheters mentioned above display a series of cross-sectional images from which additional information can be obtained.

Catheter-mounted probes, and in particular, IVUS probes can be configured to render a variety of two and three-dimensional images. In addition to the two-dimensional transverse cross-sectional images discussed above, a longitudinal planar image can be constructed from a plane which cuts through a "stack" of cross-section "slices". In addition, three-dimensional "fly-through" images can be constructed from information in a series of cross-sectional slices of a vessel. Though these three-dimensional images can be visually impressive, the two dimensional angiography image remains the primary basis for determining the location of a catheter in a vessel, and the "schematic" reference through which the physician plans and carries out a treatment procedure.

In creating the "stack" or "flythrough" images, some assumptions are made by image data processing software in terms of the orientation of each slice to the next. In many cases the compound images, rendered from a series of transverse cross-sectional slices, are rendered in the form of a straight vessel segment. In reality, vessels can curve significantly. In segment visualizations that render straight segments, spatial orientation of each cross-sectional slice in relation to other slices is not measured. In addition, the rotational orientation of a catheter-mounted probe is generally not known due to twisting of the catheter as it passes through a vessel. Therefore, the angular relation between adjacent slices is not generally known. In many cases, these limitations do not significantly effect treatment of a diseased vessel because the typical treatment modalities (balloons, stents) are not circumferentially specific. A balloon, for example, dilates a vessel 360° around a lumen.

In view of the advantages provided by the two above described methods of imaging vessels, many catheter labs use both methods simultaneously to diagnose and treat a patient. However, an angiographic image provided on a different display monitor than a corresponding IVUS image (or the other image rendered by a catheter-mounted probe), presents challenges to a obtaining a comprehensive understanding of a state of a diseased vessel. For example, a physician identifies specific structures (e.g. feeder vessels) in cross-sectional images in order to determine a location on a vessel presented on an angiography display that needs to be treated. Coordinating images rendered by two distinct display devices can become cumbersome as the physician refers back and forth between two different screens on two distinct display devices. In addition, when a video loop of IVUS images is recorded, to be played back later on a machine, a corresponding angiographic image is not recorded in sync with it. Therefore, during playback, the specific cross-section being viewed needs to be compared to the vessel angiography, which is usually on a separate file.

A known visualization display simultaneously provides an angiogram, an IVUS transverse plane view, and an IVUS longitudinal plane view. A red dot is placed upon the angiogram corresponding to a currently displayed IVUS transverse plane view. A blue line is placed upon the angiogram corresponding to a currently displayed longitudinal plane view. The reference dot and line are only as valuable as the accuracy of the process that registers their positions on the angiogram.

SUMMARY OF THE INVENTION

In order to provide a better overall view of vascular systems, in accordance with the present invention, a system and method include a single display simultaneously providing a first view of a patient including an angiogram image and a second view including an intravascular image rendered from information provided by an imaging probe mounted on a distal end of a flexible elongate member. A cursor, having a position derived from image information provided by a radiopaque marker proximate the imaging probe, is displayed within the angiogram image to correlate the position of the imaging probe to a presently displayed intravascular image and thus provide an easily discernable identification of a position within a patient corresponding to a currently displayed intravascular image. The resulting composite display simultaneously provides: an intravascular image that includes information about a vessel that is not available from an angiogram and a current location within a vessel of a source of intravascular image data from which the intravascular image is rendered.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

DETAILED DESCRIPTION OF THE DRAWINGS

In accordance with embodiments of the present invention, a method and system are described by way of example herein below including image data acquisition equipment and data/image processors that generate views on a single display that simultaneously provides positional information and intravascular images associated with a imaging probe (e.g., an IVUS transducer probe) mounted upon a flexible elongate member (e.g, a catheter, guidewire, etc.).

Figure 1:
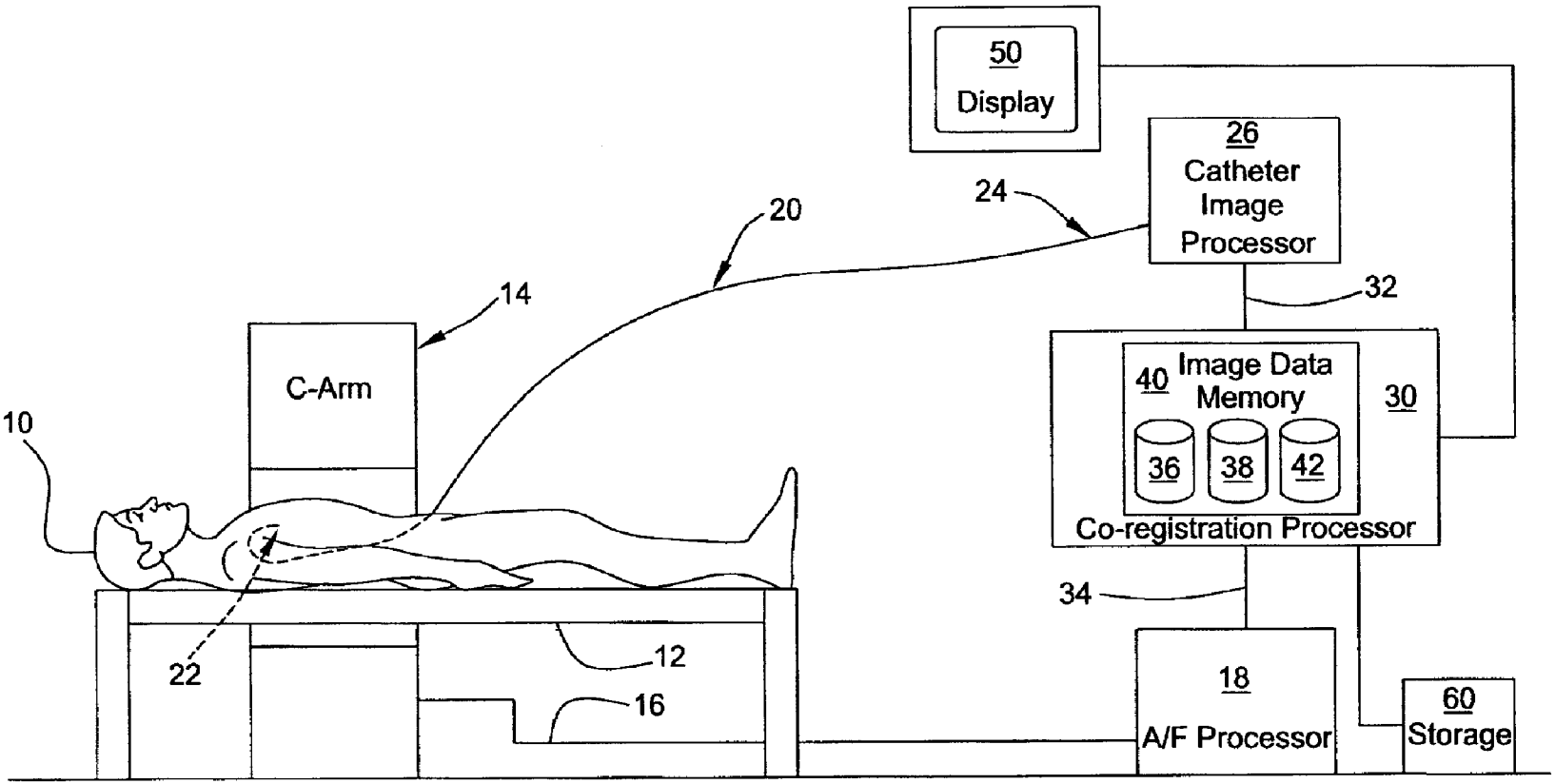
FIG. 1 is a schematic illustration of a system for implementing catheter image co-registration.

Turning initially to FIG. 1, an exemplary system is schematically depicted for carrying out the present invention in the form of co-registration of angiogram/fluoroscopy and intravascular ultrasound images. The radiological and ultrasound image data acquisition sub-systems are generally well known in the art. With regard to the radiological image data, a patient 10 is positioned upon an angiographic table 12. The angiographic table 12 is arranged to provide sufficient space for the positioning of an angiography/fluoroscopy unit c-arm 14 in an operative position in relation to the patient 10 on the table 12. Radiological image data acquired by the angiography/fluoroscopy c-arm 14 passes to an angiography/fluoroscopy processor 18 via transmission cable 16. The angiography/fluoroscopy processor 18 converts the received radiological image data received via the cable 16 into angiographic/fluoroscopic image data. The angiographic/fluoroscopic ("radiological") image data is initially stored within the processor 18.

With regard to portions of the system associated with acquiring ultrasound image data, an imaging catheter 20, and in particular an IVUS catheter, is inserted within the patient 10 so that its distal end, including a diagnostic probe 22 (in particular an IVUS probe), is in the vicinity of a desired imaging location of a blood vessel. While not specifically identified in FIG. 1, a radiopaque material located near the probe 22 provides indicia of a current location of the probe 22 in a radiological image. By way of example, the diagnostic probe 22 generates ultrasound waves, receives ultrasound echoes representative of a region proximate the diagnostic probe 22, and converts the ultrasound echoes to corresponding electrical signals. The corresponding electrical signals are transmitted along the length of the imaging catheter 20 to a proximal connector 24. IVUS versions of the probe 22 come in a variety of configurations including single and multiple transducer element arrangements. In the case of multiple transducer element arrangements, an array of transducers is potentially arranged: linearly along a lengthwise axis of the imaging catheter 20, curvilinearly about the lengthwise axis of the catheter 20, circumferentially around the lengthwise axis, etc.

The proximal connector 24 of the catheter 20 is communicatively coupled to a catheter image processor 26. The catheter image processor 26 converts the signals received via the proximal connector 24 into, for example, cross-sectional images of vessel segments. Additionally, the catheter image processor 26 generates longitudinal cross-sectional images corresponding to slices of a blood vessel taken along the blood vessel's length. The IVUS image data rendered by the catheter image processor 26 is initially stored within the processor 26.

The type of diagnostic imaging data acquired by the diagnostic probe 22 and processed by the catheter image processor 26 varies in accordance with alternative embodiments of the invention. In accordance with a particular alternative embodiment, the diagnostic probe 22 is equipped with one or more sensors (e.g., Doppler and/or pressure) for providing hemodynamic information (e.g., blood flow velocity and pressure)—also referred to as functional flow measurements. In such alternative embodiments functional flow measurements are processed by the catheter image processor 26. It is thus noted that the term "image" is intended to be broadly interpreted to encompass a variety of ways of representing vascular information including blood pressure, blood flow velocity/volume, blood vessel cross-sectional composition, shear stress throughout the blood, shear stress at the blood/blood vessel wall interface, etc. In the case of acquiring hemodynamic data for particular portions of a blood vessel, effective diagnosis relies upon the ability to visualize a current location of the diagnostic probe 22 within a vasculature while simultaneously observing functional flow metrics indicative of cardiovascular disease. Co-registration of hemodynamic and radiological images facilitates precise treatment of diseased vessels. Alternatively, instead of catheter mounted sensors, the sensors can be mounted on a guidewire, for example a guidewire with a diameter of 0.018" or less. Thus, in accordance with embodiments of the present invention, not only are a variety of probe types used, but also a variety of flexible elongate members to which such probes are mounted at a distal end (e.g., catheter, guidewire, etc.).

A co-registration processor 30 receives IVUS image data from the catheter image processor 26 via line 32 and radiological image data from the radiological image processor 18 via line 34. Alternatively, the communications between the sensors and the processors are carried out via wireless media. The co-registration processor 30 renders a co-registration image including both radiological and IVUS image frames derived from the received image data. In accordance with an embodiment of the present invention, indicia (e.g., a radiopaque marker artifact) are provided on the radiological images of a location corresponding to simultaneously displayed IVUS image data. The co-registration processor 30 initially buffers angiogram image data received via line 34 from the radiological image processor 18 in a first portion 36 of image data memory 40. Thereafter, during the course of a catheterization procedure IVUS and radiopaque marker image data received via lines 32 and 34 is stored within a second portion 38 and a third portion 42, respectively, of the image data memory 40. The individually rendered frames of stored image data are appropriately tagged (e.g., time stamp, sequence number, etc.) to correlate IVUS image frames and corresponding radiological (radiopaque marker) image data frames. In an embodiment wherein hemodynamic data is acquired rather than IVUS data, the hemodynamic data is stored within the second portion 38.

In addition, additional markers can be placed on the surface of the patient or within the vicinity of the patient within the field of view of the angiogram/fluoroscope imaging device. The locations of these markers are then used to position the radiopaque marker artifact upon the angiographic image in an accurate location.

The co-registration processor 30 renders a co-registration image from the data previously stored within the first portion 36, second portion 38 and third portion 42 of the image data memory 40. By way of example, a particular IVUS image frame/slice is selected from the second portion 38. The co-registration processor 30 identifies fluoroscopic image data within the third portion 42 corresponding to the selected IVUS image data from the second portion 38. Thereafter, the co-registration processor 30 superimposes the fluoroscopic image data from the third portion 42 upon the angiogram image frame retrieved from the first portion 36. Thereafter, the co-registered radiological and IVUS image frames are simultaneously displayed, along-side one another, upon a graphical display device 50. The co-registered image data frames driving the display device 50 are also stored upon a long-term storage device 60 for later review in a session separate from a procedure that acquired the radiological and IVUS image data stored in the image data memory 40.

While not shown in FIG. 1, a pullback device is incorporated that draws the catheter 20 from the patient at a controlled/measured manner. Such devices are well known in the art. Incorporation of such devices facilitates calculating a current position of the probe 22 within a field of view at points in time when fluoroscopy is not active.

Figure 2:
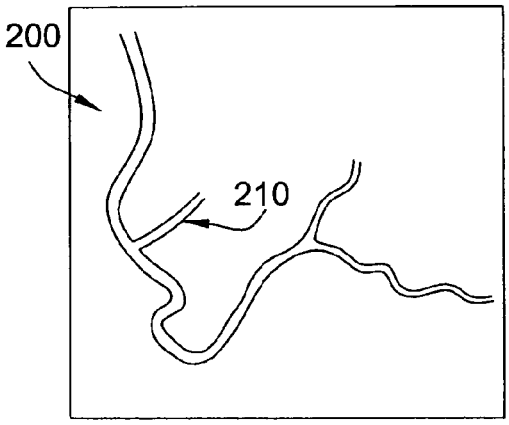
FIG. 2 depicts an illustrative angiogram image.

Turning to FIG. 2, the angiography/fluoroscopy processor 18 captures an angiographic "roadmap" image 200 in a desired projection (patient/vessel orientation) and magnification. By way of example, the image 200 is initially captured by an angiography procedure performed prior to tracking the IVUS catheter to the region of interest within a patient's vasculature. Performing the angiography procedure without the catheter 20 in the vessel provides maximal contrast flow, better vessel filling and therefore a better overall angiogram image. Thus, side branches such as side branch 210 and other vasculature landmarks can be displayed and seen clearly on the radiological image portion of a co-registered image displayed upon the graphical display device 50.

Figure 3:
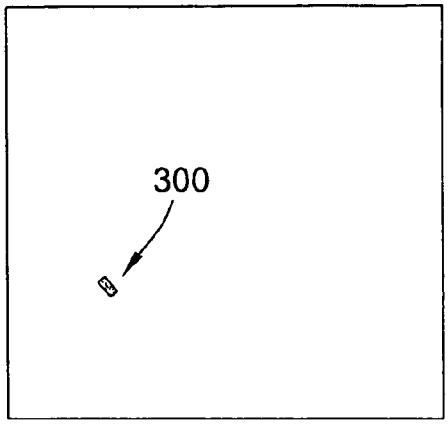
FIG. 3 depicts an illustrative fluoroscopic image of a radiopaque marker mounted upon a catheter.

Turning to FIG. 3, the catheter 20 is tracked to its starting position (e.g., a position where an IVUS pullback procedure begins). Typically the catheter 20 is tracked over a previously advanced guidewire (not shown). Thereafter, a fluoroscopic image is obtained. In the image, the catheter radiopaque marker 300 is visualized, but the vessel lumen is not, due to the absence of contrast flow. However, a set of locating markers present in both the angiogram and fluoroscopy images enable proper positioning (superimposing) of the marker image within the previously obtained angiogram image. Other ways of properly positioning the radiopaque marker image within the field of view of the angiogram image will be known to those skilled in the art in view of the teachings herein. Furthermore, the marker artifact can be automatically adjusted (both size and position) on the superimposed image frames to correspond to the approximate position of the transducers. The result of overlaying/superimposing the radiopaque marker artifact upon the angiogram image is depicted, by way of example in an exemplary co-registration image depicted in FIG. 4.

Figure 4:
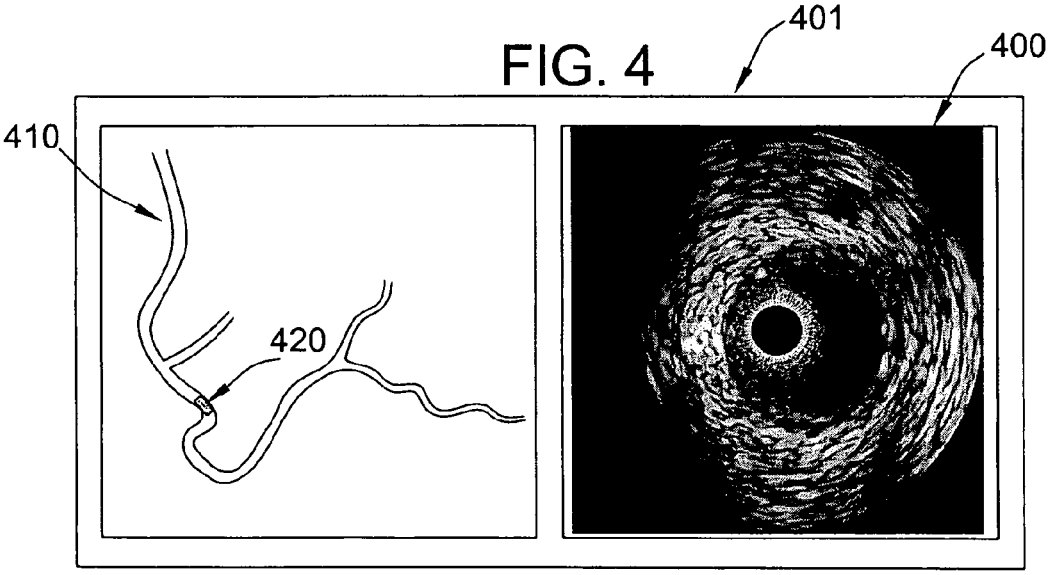
FIG. 4 depicts an illustrative enhanced radiological image along-side a cross-sectional IVUS image.

Turning to FIG. 4 the exemplary co-registration display 401 (including the correlated radiological and IVUS images) depicts a selected cross-sectional IVUS image 400 of a vessel. A radiological image 410 is simultaneously displayed along-side the IVUS image 400 on the display 50. The radiological image 410 includes a marker artifact 420, generated from radiological image data rendered by a fluoroscope image frame, superimposed on an angiogram background rendered from the first portion 36 of the memory 40. The fluoroscope image frame corresponds to the current location of the diagnostic probe 22 within a vessel under observation. Precise matching of the field of view represented in both the angiogram and fluoroscope images (i.e., precise projection and magnification of the two images) allows identification of the current position of the IVUS probe corresponding to the displayed IVUS image 400 in the right pane of the co-registered images displayed in FIG. 4.

Alternatively, the composite radiological image 410 is obtained in one step. In such case, the original roadmap angiogram image is obtained with the catheter already in its starting position. However, once obtained, the angiogram image is reused as the IVUS probe is withdrawn from the vessel.

The system also takes heart motion into account when generating/acquiring the radiological and IVUS image data. By way of example, by acquiring the image data for both the angiogram (background) and the radiopaque marker only during the peak R-wave of the EKG, heart motion is much less a factor and good overlay correlation exists between the angiogram and fluoroscope fields of view. The peak R-wave is selected because it represents end-diastole, during which the heart has the least amount of motion, and thus, a more consistent condition from which to obtain the radiological image data. The peak R-wave is also an easy point in the EKG for the system to detect.

With continued reference to FIG. 4, in an exemplary embodiment when the IVUS catheter 20 begins to image, the cross-sectional image 400 from the IVUS catheter is displayed in tandem with the enhanced radiological image 410 including both the angiogram background and the superimposed marker artifact 420. The enhanced radiological image 410 and the cross-sectional IVUS image 400 are displayed close to (e.g., along side) each other on the display 50, so that the operator can concentrate on the information in the cross-sectional image 400 while virtually simultaneously observing the status of the enhanced radiological image 410.

The simultaneous display of both the composite/enhanced radiological image and the cross-sectional image allows instant awareness of both disease state of a vessel segment and the location of the vessel segment within a patient. Such comprehensive information is not readily discernable in a three dimensional flythrough image or a stacked longitudinal image. Neither flythrough nor stacked images alone allows for the simultaneous appreciation of 1) all of the information in a cross-section, 2) a feel for the shape of the vessel and 3) the location of the cross-section along the length of the vessel. The above-described "co-registration" of enhanced angiographic (including the marker artifact) and intravascular cross-sectional images/information delivers all three of these items in a presentation that is straight forward to an operator with even average visual and spatial abilities. The co-registration display is presented, by way of example, either on an IVUS console display, or the co-registration display is presented on one or more angiographic monitors, either in the room where the procedure is occurring or in a remote location. For example, one monitor over the table in the procedure room allows the attending physician to view the procedure, while at the same time a second consulting physician who has not scrubbed for the case is also able to view the case via a second monitor containing the co-registration display from a separate control room. Control room viewing is also possible without having to wear leaded covering.

With regard to the persistence of the background angiogram ("roadmap") image portion of the enhanced radiological image 410, a single angiogram image is, by way of example, obtained/generated and stored in the first portion 36 of the memory 40 for a given procedure/patient position. If the field of view changes or the patient's position changes, then an updated background angiogram image is generated and stored in the first portion 36. Alternatively, the background angiogram image is live or continuously updated, for example, at each additional step in which angiography is performed. The projection of the angiogram roadmap/background image portion of the enhanced radiological image 410 is preferably in an orientation and magnification that best displays the entire vessel to be viewed, taking into account the foreshortening that is present in a tortuous/winding vessel. Alternatively, two roadmap images (or even two enhanced radiological images 410) can be used/displayed in place of the one image 410. Such multiple views are provided in the context of biplane angiography.

Establishing a position for the marker artifact within the field of the enhanced radiological image, based at least in part upon a radiopaque marker on the imaging catheter 20 is achievable in a variety of ways. Examples, described further herein below include: user-specified points (by clicking at a position near the marker to establish a point); image pattern recognition (automatic identification of a marker's unique signature within a field of view); and combinations of manual and automated calculations of a path.

Enhancing the background/roadmap angiogram image to render the image 410 is achieved in a number of different ways. As mentioned above, in an illustrative embodiment, the marker artifact 420 (derived from a fluoroscope image of a radiopaque marker near the probe 22 mounted on the distal end of the catheter 20) is superimposed upon/overlays the angiogram/roadmap background of the enhanced radiological image 410. Because the live/marker artifact portion of the image 410 requires that fluoroscopy be performed the entire time of catheter movement (e.g. pullback), in an alternative embodiment, the marker artifact is displayed on the image 410 only during those periods when the fluoroscope is active. When the fluoroscope is inactive, only the background angiogram is presented on the enhanced image 410 of the display 50.

Figure 5:
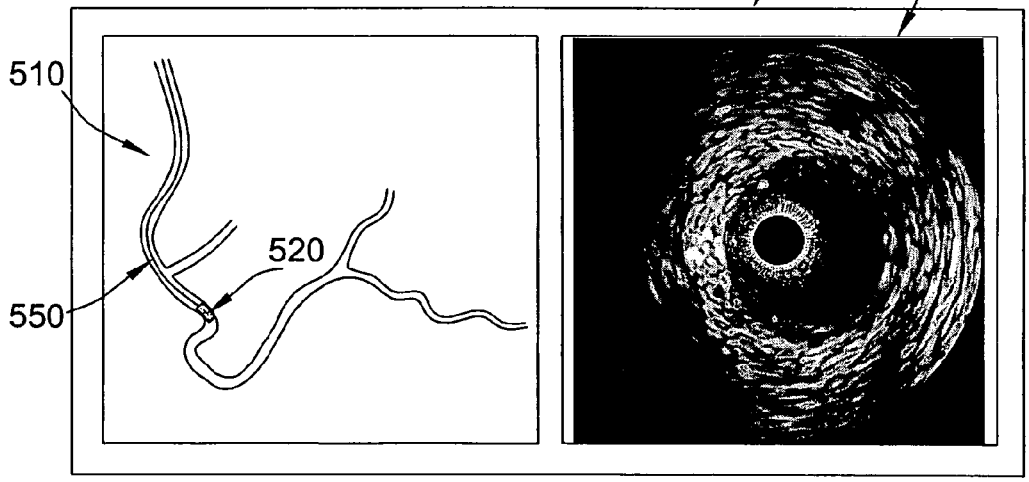
FIG. 5 depicts an illustrative enhanced radiological image along-side a cross-sectional IVUS image wherein the radiological image further includes a calculated path within a vessel of interest.
Figure 6:
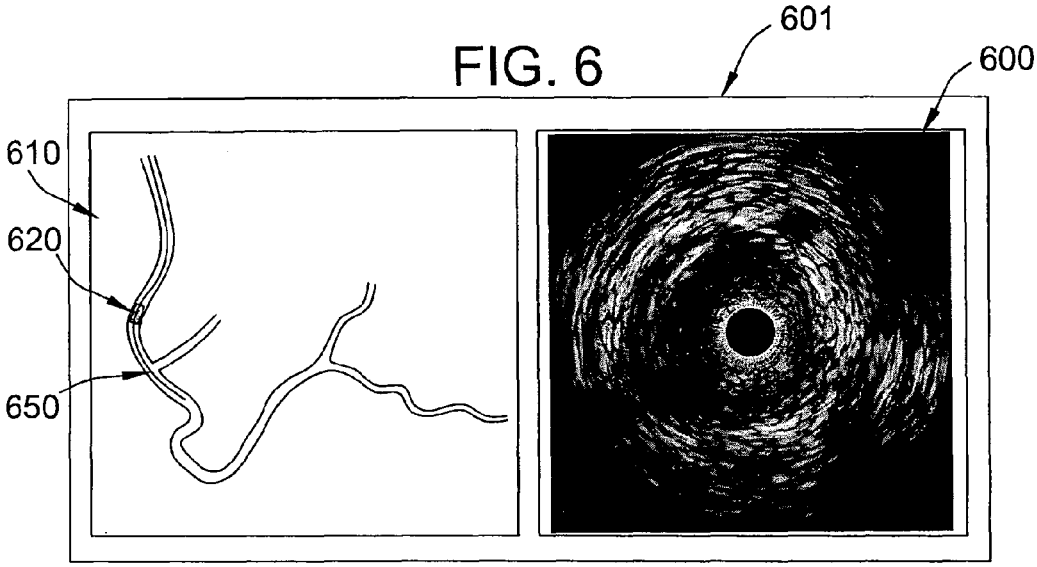
FIG. 6 depicts an illustrative enhanced radiological image along-side a cross-sectional IVUS image wherein the radiological image further includes a calculated path within a vessel of interest with a marker positioned at a different location than the view of FIG. 5.

Turning to FIGS. 5 and 6, in embodiments of the invention, when the fluoroscope is inactive, the co-registration processor 30 calculates an approximate location of the radiopaque marker based upon its last registered position and other indicators of catheter movement (e.g., pullback distance sensors/meters). The approximate location is utilized in place of the radiopaque marker image to render a marker artifact 520 on an enhanced radiological image 510 displayed along-side a corresponding IVUS cross-sectional image 500 within a display 501. By way of a particular illustrative example, during periods in which a fluoroscope is inactive, the marker artifact 520's position is calculated by software/hardware within the co-registration processor 30 from sensor data indicative of a current/changed location of the radiopaque marker within the current image field provided by the current background angiogram image. In an embodiment of the invention, a visual characteristic (e.g., color, symbol, intensity, etc.) of the marker artifact 520 is used to distinguish when the fluoroscope is active/inactive and thus indicate whether the marker artifact position is actual/calculated. Furthermore, in more advanced systems, both the displacement and angular orientation of the marker (and thus the diagnostic probe 22) are determined to render accurate approximations of the current position of the diagnostic probe 22 within a vessel as it acquires data for generating the image 500.

With continued reference to FIGS. 5 and 6, a calculated path 550/650 is determined by the co-registration processor 30 within displays 501/601. A marker artifact 520/620 is placed on top of the calculated path 550/650. The marker artifact 520/620 is superimposed on the angiogram image at a location calculated from non-visual position data (e.g., pullback distance, spatial position sensors, angular orientation sensors, etc.). For example, if the initial location of a radiopaque marker within the enhanced radiological image 510/610 is known and the catheter is pulled by an automatic pullback system at a specific rate for a known amount of time, the cursor can be placed by the system at a distance from the initial location along the calculated path 550/650 that represents the product of the pullback rate and the time period. Furthermore, each subsequent time that a fluoroscope is activated and an image of the radiopaque marker is acquired and presented to the co-registration processor 30, an error between the actual radiopaque marker location and a current calculated marker artifact 520/620 location is eliminated by replacing the calculated position by a position calculated by the radiopaque marker image. The error between the corrected position and the calculated location of the marker artifact 520/620 is determined. In an exemplary embodiment, the error/total travel distance ratio is used as a scaling factor to recalculate and adjust all previously calculated/rendered/presented marker artifact overlay positions on the rendered/stored copies of the enhanced radiological image 510/610 for the entire preceding period in which the fluoroscope has been inactive.

Similarly, a re-calculation can also update a shape of the calculated path 550/560 curve. As seen in FIGS. 5 and 6, the calculated path 550/650 is shown as a curve that matches the tortuosity of a vessel through which the probe 22 passes—represented by a center line through the displayed vessel. Alternatively, the catheter paths within vessels take a straighter and shorter path than the centerline of a blood vessel when pulled through such vessel. If, however, the catheter is being translated by pushing, instead of pulling, the calculated path 550/650 more closely matches the curvature of the vessel, or even exaggerates the tortuosity of the vessel by taking a longer path. A multiplication coefficient (e.g., 1.05 for pushing, 0.95 for pulling) can be introduced when calculating a path based upon this general observation of the path taken by a probe as it is pushed/pulled through a vessel. The path can alternatively be calculated from two different angiographic images taken at different projections (planes). This allows a three dimensional angiographic image, from which a true centerline can be calculated.

Figure 7:
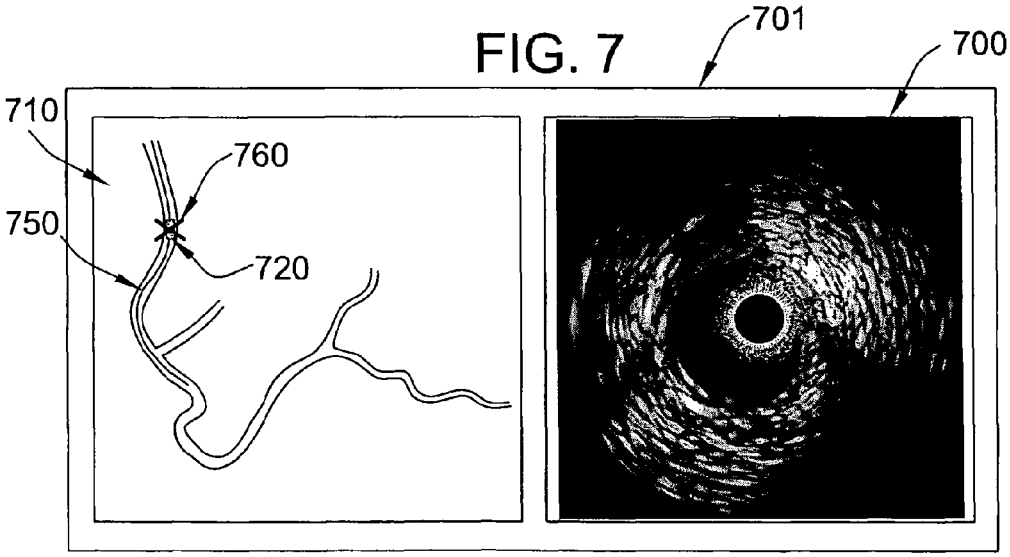
FIG. 7 depicts an illustrative enhanced radiological image along-side a cross-sectional IVUS image wherein the radiological image further includes a calculated path within a vessel of interest and a reference mark providing a point of synchronization/calibration of a marker position.

In accordance with yet another embodiment, represented by the co-registered IVUS image 700 and enhanced radiological image 710 in a display 701 presented in FIG. 7, the operator creates a reference mark 760 at one or more points on a calculated path 750. The reference mark 760 serves a variety of potential uses. By way of example, the reference mark 760 potentially serves as a benchmark (location synchronization point) for updating position of a marker artifact 720 within the enhanced radiological image 710. In the embodiment represented by FIG. 7, the co-registration processor 30 waits for manual input of the reference mark 760 location information prior to proceeding with calculations. The user creates the reference mark 760 which coincides with a marker artifact 720 rendered from image data provided by a fluoroscope of a field of view containing a radiopaque marker. The reference mark 760, which potentially persists beyond its initial entry period, is distinguished from the marker artifact 720 which follows the current/estimated position of the probe 22. Furthermore, in an exemplary embodiment the reference mark is used to highlight/mark actual positions of the probe 22 (rendered by a fluoroscope image of a radiopaque marker) as opposed to estimated points on a calculated point (e.g. points on a path e.g., 550/560) from merely calculated position estimates upon the paths 550/560. In yet other embodiments, the reference mark 760 is used to highlight a particular point of interest during a diagnostic/treatment procedure. A bookmark is placed within a series of cross-sectional images associated with the IVUS image 700 portion of the display 701. The bookmark allows quick access to a particular archived image frame corresponding to the reference mark 760 in the display 701.

In accordance with embodiments of the present invention, a user interface associated with the displayed images provided in FIGS. 4-7 includes a "slider" control that allows an operator to track through a series of stored frames representing sequentially acquired data along a traversed path within a vessel. The slider control can be a set of arrows on a keyboard, a bar/cursor displayed upon an enhanced radiological image that can be manipulated by an operator, during playback, using a mouse or other user interface device to traverse a vessel segment, etc. By way of example, a display similar to FIG. 7 is rendered by the co-registration processor 30 during playback of a previous data acquisition session. A cursor similar to the reference mark 760 is displayed during playback on the enhanced radiological image 710. A user selects and drags the cursor along a path similar to the calculated path 750. As the user drags and drops the cursor along the path, the co-registration processor 30 acquires and presents corresponding co-registered images. The user sequentially proceeds through the stored images using, by way of example, arrow keys, mouse buttons, etc.

Figure 8:
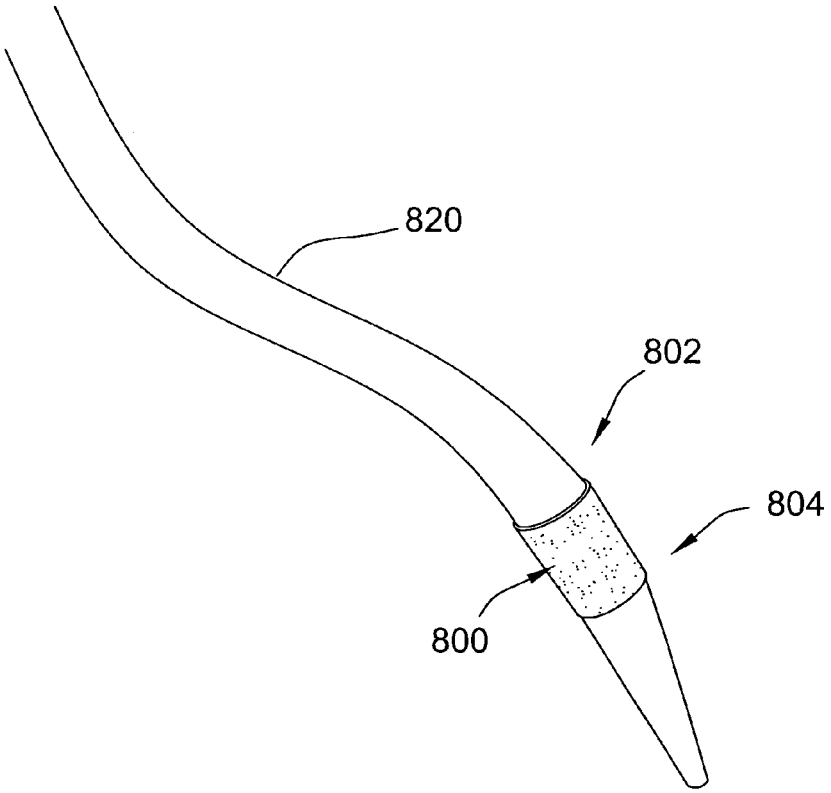
FIG. 8 depicts an illustrative catheter distal end including a single cylindrical radiopaque marker band.

It is noted that various catheter marking schemes are contemplated that improve/optimize the co-registration processor 30's calculations of a position of the marker artifact (representing a position within a vessel corresponding to a currently displayed IVUS cross-section image) when the fluoroscope is inactive. Turning to FIG. 8, a single radiopaque marker band 800 is attached to the catheter 820 near an IVUS probe. The radiopaque band 800 includes a proximal edge 802 and a distal edge 804. The band 800 is cylindrical, with the diameter at the proximal edge 802 equal to the diameter at the distal edge 804. In addition, the band 800 has a known length.

Upon connection of the proximal connector 24 of the catheter 20 into an outlet on the catheter image processor 26 (or an interposed patient interface module which is communicatively connected to the processor 26), the processor 26 receives identification information from the catheter 20 via EPROM, RFID, optical reader or any other appropriate method for identifying the catheter 20. In an illustrative embodiment, the catheter length and diameter dimensions (or dimension ratio) are included in the received identification information. In addition, image field information such as magnification and/or projection angle) from the radiological image processor 18 is provided to the co-registration processor 30. By identifying four points at the corners of an approximate four-sided polygon of the marker band image, the co-registration processor 30 automatically calculates foreshortening of a vessel in an enhanced radiological image view and the true length of a segment of a calculated path.

Figure 9A:
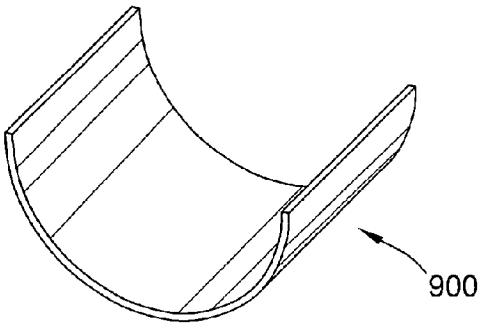
FIG. 9a depicts a radiopaque marker band 900, suitable for use in an exemplary embodiment, that partially encircles the catheter shaft.

Turning briefly to FIGS. 9a-e, a catheter 920 carries two marker bands having a known linear separation distance that facilitates making the calculations described herein above with reference to FIG. 8. FIG. 9a shows a radiopaque marker band 900, suitable for use in an exemplary embodiment, that partially encircles the catheter shaft; In the exemplary embodiment, the marker band 900 extends about 180° (one half) of the perimeter of the catheter shaft. The band is potentially made, for example, of 100% Platinum, or 90% Platinum/10% Irridium, Tantalum, Gold or any other radiopaque materials or combinations/amalgams thereof.

Figure 9B:
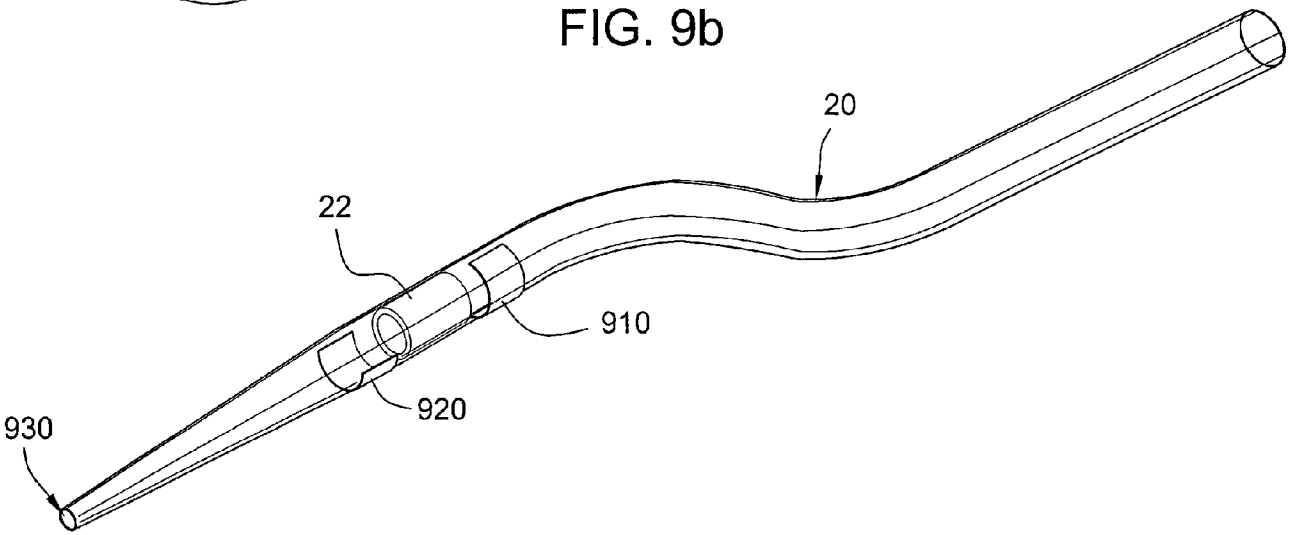
FIG. 9b depicts an imaging catheter having two of the radiopaque marker bands of the type depicted in FIG. 9a wherein the two bands are skewed by a quarter rotation along the axis of the catheter.

FIG. 9b shows an imaging catheter 20 having two of the radiopaque marker bands 910 and 920 of the type depicted in FIG. 9a. The proximal band 910 is skewed 90° (a quarter of the circumference of the catheter 20) in relation to the distal band 920. In this embodiment, the bands 910/920 are shown equally spaced on opposite sides of the diagnostic probe 22 . This catheter 20 also has a guidewire lumen 930 for passing a guidewire, for example a 0.014" guidewire. The guidewire exits out the distal guidewire port. The proximal end of the guidewire can exit a proximal port either within the blood vessel (short lumen rapid exchange catheter), within a guiding catheter (long lumen rapid exchange catheter) or outside of the patient (over-the-wire catheter).

Figures 9C, 9D, 9E:
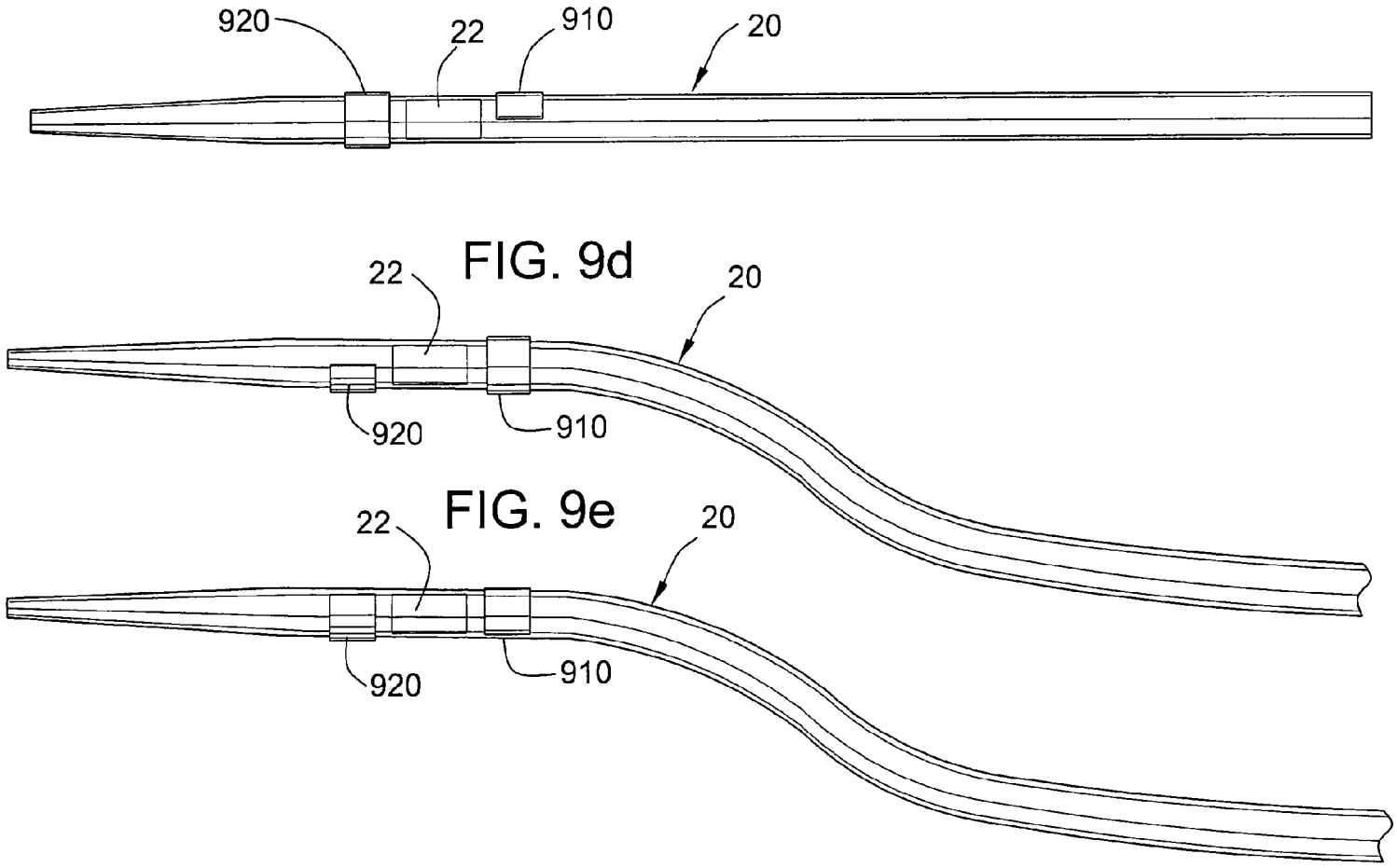
FIG. 9c depicts the imaging catheter of 9b from a view that looks directly on the full surface of the distal marker band 920.
FIG. 9d depicts the imaging catheter of 9c at a view wherein the catheter is axially rotated 90 degrees from the position depicted in FIG. 9c.
FIG. 9e depicts the imaging catheter at a different rotational position from FIG. 9c and FIG. 9d.

FIG. 9c shows the imaging catheter 20 from a view that looks directly on the full surface of the distal marker band 920. Exactly one half of the proximal marker band 910, skewed by 90 degrees, is seen. An angiography image of the two marker bands, when viewed as shown in FIG. 9c reveals band 920 having a thickness that is twice the thickness of the image of the band 910. Furthermore, an image length "L" of the marker bands 910/920 depends on angular position of the portion of the catheter 20 in the image containing the bands 910/920. In a perfect side view, the length L is equal to the actual length of the marker band. Offset O is equal to the difference between the thickness of band 920 and the thickness of band 910.

In FIG. 9d an image is taken at a view wherein the catheter 20 is axially rotated 90 degrees from the position depicted in FIG. 9c. The thickness of band 920 is half the thickness of band 910. Also, the position of the relative positions of the bands 910/920 in relation to the axis of the catheter 20 is used to determine the actual angular orientation of the catheter 20 since the offset alone is not enough to establish a current rotational position of the catheter 20.

FIG. 9e is an image of the catheter 20 and bands 910/910 at a different rotational position from FIG. 9c and FIG. 9d. The orientation of the catheter can be determined by comparing the relative thicknesses (e.g., the offset, a ratio) of the thickness of images of the bands 910 and 920.

Other controls associated with the co-registration processor 30 facilitate performing a variety of additional tasks. For example, during a catheter pullback, a commenting functionality incorporated into the processor 30 enables a user to select a "bookmark" button. In response, the co-registration processor 30 attaches a note/comment to a specific cross-section and/or location along a calculated path on an enhanced radiological image.

As mentioned above, an alternative version of co-registration image scheme incorporates biplane angiography instead of standard, single view angiography images. In biplane angiography, two radiological projections are simultaneously presented to a user—e.g., two views skewed by 90 degrees on a common axis of rotation. In such systems, two enhanced radiological images are presented along-side a cross-sectional image. During an inactive fluoroscopy period, when marker artifact (cursor) position is determined by calculations in relation to a known pullback rate, two cursor positions are determined—one on each of the two enhanced radiological images. It is expected that at certain periods during which fluoroscopy is inactive, the foreshortening of the vessel seen on one biplane image is less than the other. Depending on the 3-dimensional vessel tortuosity, it is expected that the opposite biplane image would have less foreshortening at other periods where a marker artifact is based upon calculations rather than actual fluoroscope images. The errors are calculated independently in the two different biplane images, and corresponding scaling factors are generated for the correction. As previously mentioned, a derived 3-dimensional roadmap is created based on information of the two images from different planes. In this case, the two different planes are the 90° biplane images Locating a marker artifact on a derived 3-D image is calculated from locations of marker artifacts one each of two orthogonal biplane images.

All of the descriptions hereinabove associated with illustrative embodiments using an IVUS catheter are applicable to a variety of alternative types of imaging catheters. Similarly, an enhanced radiological image can be combined with a longitudinal stack instead of a cross sectional slice—in fact, the enhanced radiological, transverse cross-sectional, and longitudinal cross-sectional images can be displayed together. In yet other embodiments, the enhanced radiological image is presented along-side an IVUS image including both grayscale and color image artifacts that characterizing tissue and deposits within a vessel. Additionally, the longitudinal IVUS grayscale image and/or the color (Virtual Histology) image are overlaid on the 2-D angiographic image or derived 3-D image.

Figure 10:
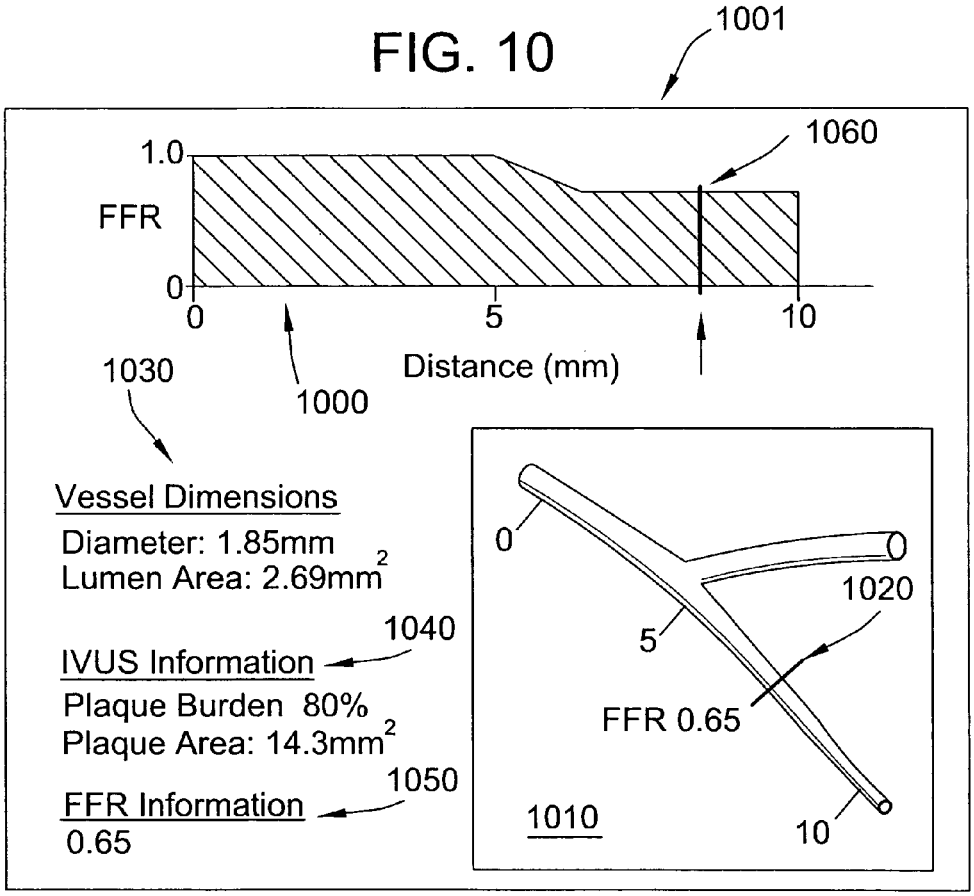
FIG. 10 depicts an illustrative display for co-registration of radiological and hemodynamic image information.

The above-described examples of co-registration have primarily addressed IVUS examples. However, as mentioned above, co-registration is alternatively incorporated into functional flow measurement systems that provide hemodynamic image information such as blood flow velocity and pressure. Turning briefly to FIG. 10, an exemplary co-registration display 1001 rendered by the co-registration processor 30 includes an enhanced radiological image 1010 displayed along-side functional flow measurement values presented in a graph 1000. In FIG. 10 functional flow reserve (FFR) is depicted in the graph 1000 as a function of displacement along a length of a blood vessel. The enhanced radiological image 1010 comprises a marker artifact 1020 superimposed upon an angiogram image. The marker artifact 1020 indicates the point at which the presently displayed functional flow measurements are being presented based upon measurements previously acquired by sensors/transducers on the probe 22 mounted at the distal end of a flexible elongate member such as a guidewire or the catheter 20. In yet another illustrative embodiment, the co-registration image further includes an IVUS cross-sectional image (not depicted) corresponding to the vessel segment indicated by the marker artifact 1020 on the enhanced radiological image 1010.

The display also includes a variety of additional text information associated with the section of the vessel identified by the marker artifact 1020. Vessel dimensions 1030 specify an approximate diameter and lumen area of a particular cross section indicated by the marker artifact 1020's current position on the enhanced radiological image 1010. Additionally, IVUS information 1040 specify a plaque burden percentage and a total plaque area for a current cross-sectional slice indicated by the marker artifact 1020. An FFR information 1050 specifies a current FFR value associated with the current location of the marker artifact 1020. It is noted that the marker artifact 1020 approximates the location of a probe (e.g., probe 22) at the time data was acquired to render the presently displayed data values. In accordance with an exemplary embodiment of the present invention, the location of the marker artifact 1020 is derived from image data provided by a radiopaque element/marker located near a probe mounted upon a flexible elongate member such as probe 22 mounted on a guidewire or catheter 20.

By way of example, the marker artifact 1020 operates as a slider control that enables a user to sequentially traverse a set of stored data records containing information of the type displayed in FIG. 10. Furthermore, in the particular example, an FFR value associated with a particular location designated by the marker artifact 1020 is displayed near the marker artifact 1020. Also, a second slider 1060 is also provided that is linked to the position of marker artifact 1020 and thus moves in synchronism with the marker artifact 1020. Moving either the slider 1060 or the marker artifact 1020 causes movement of the other.

Other types of interventional ultrasound imaging, such as Intracardiac Echocardiography are also envisioned that utilize this co-registration system. For example a steerable catheter with a linear, curvilinear, circumferential or other ultrasonic array at the distal end is placed into or in proximity to the chambers of the heart, and its location is incorporated into an enhanced ultrasound image.

Figure 11:
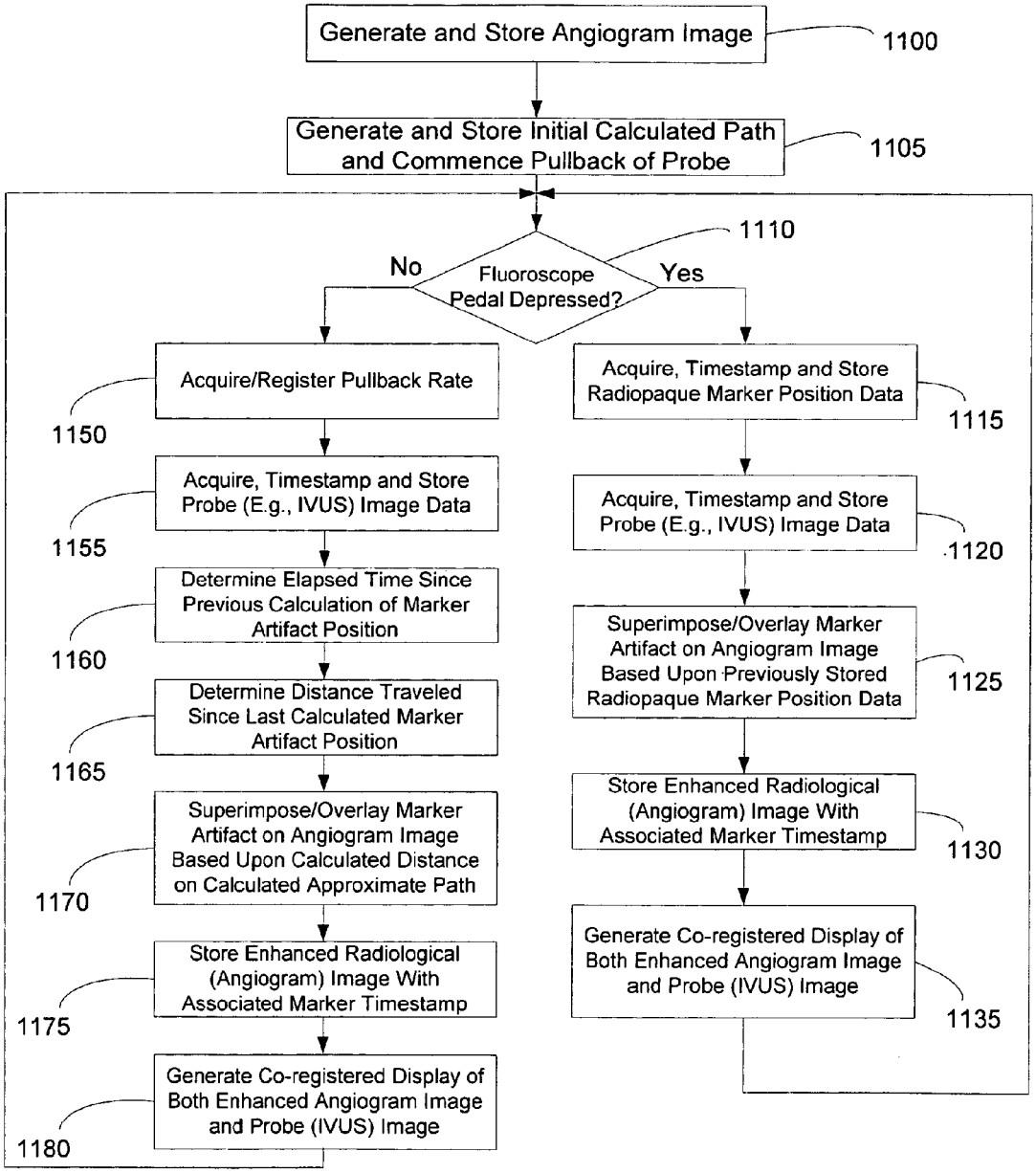
FIG. 11 is a flowchart summarizing a set of steps for rendering and displaying a co-registered view during a data acquisition procedure.

Having described exemplary systems embodying the present invention, attention is directed to FIG. 11 that summarizes a set of exemplary steps associated with the operation of the above-described systems. Initially, during step 1100 an angiogram image is generated and stored within the first portion 36 of image data memory 40. A single angiogram image can be used to support co-registered display of multiple acquired data sets from the probe 22 as the probe 22 passes within a length of a blood vessel. A visual artifact (e.g., marker artifact 420) having a position determined at least in part upon a radiopaque marker positioned near the probe 22 on the imaging catheter 20, is superimposed on the angiogram image. As the probe 22 passes within the blood vessel the visual artifact progresses along the angiogram image of the blood vessel thereby providing an approximate location of the probe 22 associated with currently displayed data rendered according to information provided by the probe 22.

Thereafter, during step 1105 an initial calculated path (e.g., path 550) is generated by the co-registration processor 30. This estimation of the path can be generated according to any of a variety of methods including: automated two-dimensional and three-dimensional path calculations; manual path specification; and user assisted automated path calculations (a combination of automated path calculation with user-specified over-rides). The calculated path is superimposed upon the angiogram image generated during step 1100 and represents the projected path of the probe 22 when pullback is commenced of the probe 22.

In an exemplary embodiment, the operation of the co-registration system is determined by whether the fluoroscope has been activated (providing a live image of a radiopaque marker mounted proximate the probe 22). If the fluoroscope is active, then control passes to step 1115 wherein a fluoroscope image (see, e.g., FIG. 3) of the radiopaque marker is acquired, timestamped and stored. Thereafter, at step 1120 image data associated with the probe 22 is acquired, timestamped and stored. In the illustrative example, the image data comprises an IVUS image generated by an ultrasound transducer probe mounted upon the imaging catheter 20.

At step 1125 the co-registration processor 30 superimposes/overlays a marker artifact on the previously stored angiogram image to render the aforementioned enhanced radiological image. The marker artifact derives is position, at least in part, from the previously acquired and stored radiopaque marker position data. The enhanced radiological (e.g., angiogram) image is thereafter stored with the timestamp associated with the radiopaque marker position data during step 1130.

Thereafter, at step 1135 the co-registration processor 30 renders and simultaneously presents on a display/monitor the previously generated enhanced angiogram image and a corresponding probe (IVUS) image. The enhanced angiogram image and the corresponding probe image are displayed along-side one another on the display/monitor. Selection of a corresponding image is based upon a timestamp associated with the selected IVUS probe image. The respective timestamps of the radiological and probe components of the co-registered display need not be identical. In an embodiment of the invention a closest match criterion is applied to the selection process. Control then returns to step 1110 for another iteration of the co-registration imaging process.

Alternatively, if the fluoroscope is inactive during a period wherein a pullback mechanism is drawing the probe 22 through a segment of a vessel of interest, then control passes from step 1110 to step 1150. At 1150 the co-registration processor 30 acquires/registers a pullback rate for the pullback mechanism. At step 1155 image data associated with the probe 22 is acquired, timestamped and stored. In the illustrative example, the image data comprises an IVUS image generated by an ultrasound transducer probe mounted upon the imaging catheter 20. During step 1160 the processor 30 determines a time that has elapsed since the previous calculation of the artifact marker position. In cases where the elapsed time is a constant, this step need not be repeated once the elapsed time constant has been determined. During step 1165 the co-registration processor 30 generates an estimate of a present position of the probe 22 and a corresponding marker artifact position on the enhanced radiological image. By way of example, the pullback rate and the elapsed time between a previous marker artifact position determination and the present position determination are used to generate a present position estimate for the marker artifact.

Thereafter, during step 1170 the co-registration processor 30 superimposes/overlays a marker artifact on the angiogram at the new calculated position based upon the calculated path and the distance calculation rendered during step 1165. During step 1175 the enhanced radiological (e.g., angiogram) image is stored with the timestamp associated with the calculated marker artifact position data. Thereafter, at step 1180 the resulting enhanced radiological image is utilized to render and present a co-registered display including both the enhanced angiogram image and a corresponding (based upon timestamp) previously stored probe image. Control thereafter returns to step 1110.

Figure 12:
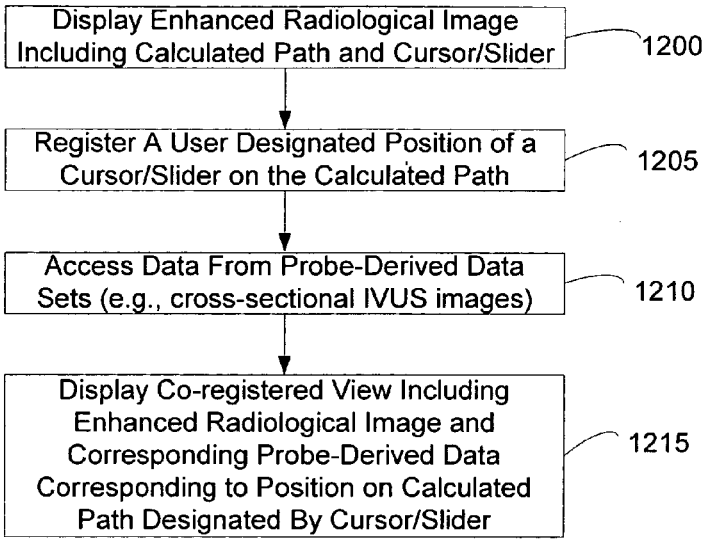
FIG. 12 is a flowchart summarizing a set of steps for rendering and displaying a co-registered view during playback of previously acquired image data.

The above-described steps are associated with providing a co-registered display as an intravascular probe mounted upon a flexible elongate member (e.g., a catheter, guidewire, etc.) progresses along a length of blood vessel. Co-registered displays are also rendered in a playback mode. Turning to FIG. 12, during step 1200 the co-registration processor 30 initially displays an enhanced radiological image including, for example, an angiogram image, a calculated path, and a cursor/slider mark positioned on the calculated path indicating a location associated with a presently provided image derived from data acquired by the probe 22 at the indicated location on the enhanced radiological image.

During step 1205 a user positions the cursor/slider mark on the calculated path. Such repositioning can occur in any of a number of ways. By way of example, the user drags and drops the cursor/slider using a mouse. Alternatively, a keyboard input can advance/backup the cursor/slider through a series of previously designated/bookmarked points along the calculated path displayed within the enhanced angiogram image provided during step 1200. Yet other keys can be used to advance the cursor/slider on a record-by-record basis through a set of stored records associated with the progression of the probe 22 along the calculated path. Still other modes of selecting a position of interest on the calculated path and its associated probe 22 (e.g., IVUS) image will be contemplated by those skilled in the art in view of the description provided herein.

During step 1210 in response to a particular position/timestamp associated with a current position of the cursor/slider on the enhanced radiological image, the co-registration processor 30 accesses a corresponding record within the set of records derived from the data provided by the probe 22. By way of example, such data sets include cross-sectional IVUS images or alternatively FFR values at specified positions along a blood vessel. Thereafter, during step 1215 a co-registered view is presented wherein the enhanced radiological image, including the calculated path and cursor/slider (derived at least partially from positional information provided by a radiopaque marker during data acquisition), is displayed along-side an image (e.g., an IVUS cross-section) derived from data provided by the probe 22 at a position indicated by the current cursor/slider position within the enhanced radiological image. The steps depicted in FIG. 12 are repeated in response to a detected change in the position of the cursor/slider to update the display to show the new position of the cursor/slider and the corresponding image (e.g. cross-sectional IVUS image) derived from data provided by the probe 22 at the designated cursor/slider position.

The structures, techniques, and benefits discussed above are merely exemplary embodiments of the invention. In view of the many possible embodiments to which the principles of this invention may be applied, it should be recognized that the embodiments described herein with respect to the drawing figures are meant to be illustrative only and should not be taken as limiting the scope of invention. For example, while separate processors are shown to carry out particular aspects of the invention, in alternative embodiments the functionality of the multiple processors can be incorporated into a single processor or even distributed among even more processors. Therefore, the invention as described herein contemplates all such embodiments as may come within the scope of the following claims and equivalents thereof.

What is claimed is:

1. A system for acquisition and co-registered display of intravascular information, comprising:

an imaging flexible elongate member having a proximal end and a distal end;

an imaging probe located near the distal end of the flexible elongate member, and configured to obtain information for generating an image of a vessel;

a radiopaque marker located near the imaging probe;

a first memory for storing angiogram image data;

a second memory for storing intravascular image data derived from information obtained by the imaging probe;

a third memory for storing radiopaque marker image data, distinct from the angiogram image data, the radiopaque marker image data being derived from information obtained from a fluoroscopic imaging device;

a display processor configured to retrieve and combine data from the first memory, the second memory and the third memory, and further configured to render a composite image including:

an enhanced radiological image derived from the angiogram image data comprising a superimposition of at least a portion of the angiogram data and the radiopaque marker image data and providing a location of the radiopaque marker based upon an actual location during active fluoroscopy and an estimated location during inactive fluoroscopy, an intravascular image element corresponding to the intravascular image data, wherein the enhanced radiological image and the intravascular image element are displayed proximate each other; and a cursor, displayed upon the enhanced radiological image, indicative of a location of the imaging probe while acquiring data for the intravascular image element presently displayed on the composite image, said cursor having a position that is based at least in part on third data derived from the radiopaque marker image data stored in the third memory;

wherein the display processor is further configured to calculate an error function based on a difference between the estimated location of the radiopaque marker and the actual location of the radiopaque marker and wherein the display processor further configured to utilize the error function to correct the estimated location of the radiopaque marker for the preceding period of inactive fluoroscopy.

2. The system of claim 1 wherein the flexible elongate member is a catheter.

3. The system of claim 1 wherein the imaging probe comprises an ultrasound device.

4. The system of claim 3 wherein the ultrasound device is a side-firing intravascular ultrasound transducer assembly.

5. The system of claim 4 wherein the side-firing intravascular ultrasound transducer assembly comprises an array of transducer elements.

6. The system of claim 5 wherein the array of transducer elements are linearly arranged along a lengthwise axis of the flexible elongate member.

7. The system of claim 5 wherein the array of transducer elements are curvilinearly arranged about a lengthwise axis of the flexible elongate member.

8. The system of claim 5 wherein the array of transducer elements are circumferentially arranged about a lengthwise axis of the flexible elongate member.

9. The system of claim 3 wherein the ultrasound device comprises a Doppler transducer.

10. The system of claim 9 wherein the flexible elongate member comprises a guidewire.

11. The system of claim 1 wherein the flexible elongate member is a guidewire and the imaging probe comprises a pressure sensor.

12. The system of claim 1 wherein the radiopaque marker comprises a cylindrical marker band.

13. The system of claim 1 wherein the radiopaque marker comprises at least one partially complete cylindrical marker band.

14. The system of claim 13 wherein the radiopaque marker comprises two semi-cylindrical marker bands.

15. The system of claim 14 wherein the two semi-cylindrical marker bands are skewed in relation to one another along a lengthwise axis of the flexible elongate member.

16. The system of claim 15 wherein the display processor further comprises an orientation determination function for determining a relative orientation of the imaging probe within the vessel based upon at least a relative size and position of the two semi-cylindrical marker bands in relation to one another.

17. The system of claim 1 wherein the third data is derived from user-specified points.

18. The system of claim 1 wherein the third data is derived by automated processes that determine a position of the radiopaque marker within a field of view.

19. The system of claim 18 wherein the automated processes utilize image pattern recognition to determine the position.

20. The system of claim 1 wherein the third data is derived from a combination of manual user input and automated calculations.

21. The system of claim 20 wherein the automated calculations include determination of a predicted path of the imaging probe.

22. The system of claim 1 wherein the display processor further comprises a bookmark function enabling a user to designate particular images of interest in a stored set of images containing at least the intravascular image element.

23. The system of claim 1 wherein the enhanced radiological image includes a calculated path of the imaging probe.

24. The system of claim 1 wherein the display processor further comprises-a slider function associated with the cursor that enables a user to reposition the cursor to a point of interest on the enhanced radiological image through a user interface control, and in response displays a particular instance of the intravascular image element associated with the point of interest.

25. The system of claim 1, wherein the estimated location is based at least in part on a calculated path of the imaging probe and wherein the calculated path is updated based on the error function that is calculated based on a difference between the estimated location of the radiopaque marker and the actual location of the radiopaque marker.

26. A method for acquiring and displaying intravascular information in a system including an imaging flexible elongate member having a proximal end and a distal end, an imaging probe located near the distal end of the flexible elongate member, and configured to obtain information for generating an image of a vessel, and a radiopaque marker located near the imaging probe, the method comprising the steps of:

storing angiogram image data in a first memory;

storing intravascular image data derived from information obtained by the imaging probe in a second memory;

storing radiopaque marker image data, distinct from the angiogram image data, in a third memory, the radiopaque marker image data being derived from information obtained from a fluoroscopic imaging device;

combining, by a display processor, data retrieved from the first memory, the second memory and the third memory to render a composite image including:

an enhanced radiological image derived from the angiogram image data comprising a superimposition of at least a portion of the angiogram data and the radiopaque marker data and providing a location of the radiopaque marker based upon an actual location during active fluoroscopy and an estimated location during inactive fluoroscopy, and an intravascular image element corresponding to the intravascular image data, wherein the enhanced radiological image and the intravascular image element are displayed proximate each other; and displaying a cursor upon the enhanced radiological image, indicative of a location of the imaging probe while acquiring data for the intravascular image element presently displayed on the composite image, said cursor having a position that is based at least in part on third data derived from the radiopaque marker image data previously stored in the third memory;

wherein the estimated location is based on a calculated path of the imaging probe, and wherein an error function is calculated based on a difference between the estimated location of the radiopaque marker and the actual location of the radiopaque marker when active fluoroscopy is resumed after inactive fluoroscopy and wherein the error function is utilized to correct the calculated path.

27. The method of claim 26 wherein the flexible elongate member is a catheter.

28. The method of claim 26 wherein the imaging probe comprises an ultrasound device.

29. The method of claim 28 wherein the ultrasound device comprises a Doppler transducer.

30. The method of claim 26 wherein the flexible elongate member is a guidewire and the imaging probe comprises a pressure sensor.

31. The method of claim 26 wherein the radiopaque marker comprises two semi-cylindrical marker bands that are skewed in relation to one another along a lengthwise axis of the flexible elongate member and wherein the method comprises determining an orientation of the imaging probe based upon at least a relative size and position of the two semi-cylindrical marker bands in relation to one another.

32. The method of claim 26 wherein the third data is derived from user-specified points.

33. The method of claim 26 wherein the third data is derived by automated processes that determine a position of the radiopaque marker within a field of view.

34. The method of claim 26 wherein the third data is derived from a combination of manual user input and automated calculations.

35. The method of claim 34 wherein the automated calculations determine a predicted path of the imaging probe.

36. The method of claim 26 further comprising storing a user-designated set of particular images of interest in a stored set of images containing at least the intravascular image element.

37. The method of claim 26 further comprising incorporating a calculated path of the imaging probe within the enhanced radiological image.

38. The method of claim 26 further comprising providing a slider function associated with the cursor that enables a user to reposition the cursor to a point of interest on the enhanced radiological image through a user interface control, and in response display a particular instance of the intravascular image element associated with the point of interest.

39. The method of claim 26, wherein the calculated path is calculated using a first multiplication coefficient if the imaging probe is being pulled through the vessel and a second multiplication coefficient if the imaging probe is being pushed through the vessel.

40. A system for acquisition and co-registered display of intravascular information, comprising:

an imaging flexible elongate member having a proximal end and a distal end;

an imaging probe located near the distal end of the flexible elongate member, and configured to obtain information for generating an image of a vessel;

a radiopaque located near the imaging probe;

a first memory portion for storing angiogram image data;

a second memory portion for storing intravascular image data derived from information obtained by the imaging probe;

a third memory portion for storing radiopaque marker image data, the radiopaque marker image data being derived from information obtained from a fluoroscopic imaging device;

a display processor configured to retrieve and combine data from the first memory portion, the second memory portion and the third memory portion, and further configured to render a composite image including:

an enhanced radiological image derived from the angiogram image data comprising a superimposition of at least a portion of the angiogram data and the radiopaque marker image data and providing a location of the radiopaque marker based upon an actual location during active fluoroscopy and an estimated location during inactive fluoroscopy, wherein an error function is calculated based on a difference between the estimated location of the radiopaque marker and the actual location of the radiopaque marker when active fluoroscopy is resumed after inactive fluoroscopy and wherein the error function is utilized to correct the estimated location of the radiopaque marker for the preceding period of inactive fluoroscopy, an intravascular image element corresponding to the intravascular image data, wherein the enhanced radiological image and the intravascular image element are displayed proximate each other; and a cursor, displayed upon the enhanced radiological image, indicative of a location of the imaging probe while acquiring data for the intravascular image element presently displayed on the composite image, said cursor having a position that is based at least in part on third data derived from the radiopaque marker image data stored in the third memory portion.

41. The method of claim 40, wherein the calculated path is calculated using a first multiplication coefficient if the imaging probe is being pulled through the vessel and a second multiplication coefficient if the imaging probe is being pushed through the vessel.

42. The system of claim 40, wherein the imaging flexible elongate member is a catheter.

43. The system of claim 40, wherein the imaging flexible elongate member is a guidewire.

44. The system of claim 40, wherein the imaging probe includes an ultrasound transducer.

45. The system of claim 40, wherein the imaging probe includes a pressure sensor.

*46. A system for acquisition and co-registered display of intravascular information, comprising:*

*a flexible elongate member having a proximal end and a distal end;*

*a diagnostic probe located near the distal end of the flexible elongate member, and configured to obtain information related to a vessel;*

*a radiopaque marker located near the diagnostic probe;*

*a first memory for storing angiogram image data;*

*a second memory for storing intravascular data derived from information obtained by the diagnostic probe;*

*a third memory for storing radiopaque marker image data, distinct from the angiogram image data, the radiopaque marker image data being derived from information obtained from a fluoroscopic imaging device;*

*a display processor configured to retrieve and combine data from the first memory, the second memory and the third memory, and further configured to render a composite image including:*

*an enhanced radiological image derived from the angiogram image data comprising a superimposition of at least a portion of the angiogram data and the radiopaque marker image data and providing a location of the radiopaque marker based upon an actual location during active fluoroscopy and an estimated location during inactive fluoroscopy,*

*an intravascular image element corresponding to the intravascular data, wherein the enhanced radiological image and the intravascular image element are displayed proximate each other; and*

*a cursor, displayed upon the enhanced radiological image, indicative of a location of the diagnostic probe while acquiring data for the intravascular image element presently displayed on the composite image, said cursor having a position that is based at least in part on third data derived from the radiopaque marker image data stored in the third memory;*

*wherein the display processor is further configured to calculate an error function based on a difference between the estimated location of the radiopaque marker and the actual location of the radiopaque marker and wherein the display processor further configured to utilize the error function to correct the estimated location of the radiopaque marker for the preceding period of inactive fluoroscopy.*

*47. The system of claim 46 wherein the flexible elongate member is a catheter.*

*48. The system of claim 46 wherein the diagnostic probe comprises an ultrasound device.*

*49. The system of claim 48 wherein the ultrasound device is a side-firing intravascular ultrasound transducer assembly.*

*50. The system of claim 49 wherein the side-firing intravascular ultrasound transducer assembly comprises an array of transducer elements.*

*51. The system of claim 50 wherein the array of transducer elements are linearly arranged along a lengthwise axis of the flexible elongate member.*

*52. The system of claim 50 wherein the array of transducer elements are curvilinearly arranged about a lengthwise axis of the flexible elongate member.*

*53. The system of claim 50 wherein the array of transducer elements are circumferentially arranged about a lengthwise axis of the flexible elongate member.*

*54. The system of claim 48 wherein the ultrasound device comprises a Doppler transducer.*

*55. The system of claim 54 wherein the flexible elongate member comprises a guidewire.*

*56. The system of claim 46 wherein the flexible elongate member is a guidewire and the diagnostic probe comprises a pressure sensor.*

*57. The system of claim 46 wherein the radiopaque marker comprises a cylindrical marker band.*

*58. The system of claim 46 wherein the radiopaque marker comprises at least one partially complete cylindrical marker band.*

*59. The system of claim 58 wherein the radiopaque marker comprises two semi-cylindrical marker bands.*

*60. The system of claim 59 wherein the two semi-cylindrical marker bands are skewed in relation to one another along a lengthwise axis of the flexible elongate member.*

*61. The system of claim 60 wherein the display processor further comprises an orientation determination function for determining a relative orientation of the diagnostic probe within the vessel based upon at least a relative size and position of the two semi-cylindrical marker bands in relation to one another.*

*62. The system of claim 46 wherein the third data is derived from user-specified points.*

*63. The system of claim 46 wherein the third data is derived by automated processes that determine a position of the radiopaque marker within a field of view.*

*64. The system of claim 63 wherein the automated processes utilize image pattern recognition to determine the position.*

*65. The system of claim 46 wherein the third data is derived from a combination of manual user input and automated calculations.*

*66. The system of claim 65 wherein the automated calculations include determination of a predicted path of the diagnostic probe.*

*67. The system of claim 46 wherein the display processor further comprises a bookmark function enabling a user to designate particular images of interest in a stored set of images containing at least the intravascular image element.*

*68. The system of claim 46 wherein the enhanced radiological image includes a calculated path of the diagnostic probe.*

*69. The system of claim 46 wherein the display processor further comprises-a slider function associated with the cursor that enables a user to reposition the cursor to a point of interest on the enhanced radiological image through a user interface control, and in response displays a particular instance of the intravascular image element associated with the point of interest.*

*70. The system of claim 46, wherein the estimated location is based at least in part on a calculated path of the diagnostic probe and wherein the calculated path is updated based on the error function that is calculated based on a difference between the estimated location of the radiopaque marker and the actual location of the radiopaque marker.*

*71. The system of claim 46, wherein the intravascular image element is a cross-sectional intravascular ultrasound (IVUS) image.*

*72. The system of claim 46, wherein the intravascular image element is a graph representing the intravascular data.*

*73. The system of claim 72, wherein the graph represents at least one of blood pressure, blood flow velocity, shear stress, and fractional flow reserve.*

*74. A method for acquiring and displaying intravascular information in a system including a flexible elongate member having a proximal end and a distal end, a diagnostic probe located near the distal end of the flexible elongate member, and configured to obtain information related to a vessel, and a radiopaque marker located near the diagnostic probe, the method comprising the steps of:*

*storing angiogram image data in a first memory;*

*storing intravascular data derived from information obtained by the diagnostic probe in a second memory;*

*storing radiopaque marker image data, distinct from the angiogram image data, in a third memory, the radiopaque marker image data being derived from information obtained from a fluoroscopic imaging device;*

*combining, by a display processor, data retrieved from the first memory, the second memory and the third memory to render a composite image including:*

*an enhanced radiological image derived from the angiogram image data comprising a superimposition of at least a portion of the angiogram data and the radiopaque marker data and providing a location of the radiopaque marker based upon an actual location during active fluoroscopy and an estimated location during inactive fluoroscopy, and*

*an intravascular image element corresponding to the intravascular data, wherein the enhanced radiological image and the intravascular image element are displayed proximate each other; and*

*displaying a cursor upon the enhanced radiological image, indicative of a location of the diagnostic probe while acquiring data for the intravascular image element presently displayed on the composite image, said cursor having a position that is based at least in part on third data derived from the radiopaque marker image data previously stored in the third memory;*

*wherein the estimated location is based on a calculated path of the diagnostic probe, and wherein an error function is calculated based on a difference between the estimated location of the radiopaque marker and the actual location of the radiopaque marker when active fluoroscopy is resumed after inactive fluoroscopy and wherein the error function is utilized to correct the calculated path.*

*75. The method of claim 74 wherein the flexible elongate member is a catheter.*

*76. The method of claim 74 wherein the diagnostic probe comprises an ultrasound device.*

*77. The method of claim 76 wherein the ultrasound device comprises a Doppler transducer.*

*78. The method of claim 74 wherein the flexible elongate member is a guidewire and the diagnostic probe comprises a pressure sensor.*

*79. The method of claim 74 wherein the radiopaque marker comprises two semi-cylindrical marker bands that are skewed in relation to one another along a lengthwise axis of the flexible elongate member and wherein the method comprises determining an orientation of the diagnostic probe based upon at least a relative size and position of the two semi-cylindrical marker bands in relation to one another.*

*80. The method of claim 74 wherein the third data is derived from user-specified points.*

*81. The method of claim 74 wherein the third data is derived by automated processes that determine a position of the radiopaque marker within a field of view.*

*82. The method of claim 74 wherein the third data is derived from a combination of manual user input and automated calculations.*

*83. The method of claim 82 wherein the automated calculations determine a predicted path of the diagnostic probe.*

*84. The method of claim 74 further comprising storing a user-designated set of particular images of interest in a stored set of images containing at least the intravascular image element.*

*85. The method of claim 74 further comprising incorporating a calculated path of the diagnostic probe within the enhanced radiological image.*

*86. The method of claim 74 further comprising providing a slider function associated with the cursor that enables a user to reposition the cursor to a point of interest on the enhanced radiological image through a user interface control, and in response display a particular instance of the intravascular image element associated with the point of interest.*

*87. The method of claim 74, wherein the calculated path is calculated using a first multiplication coefficient if the diagnostic probe is being pulled through the vessel and a second multiplication coefficient if the diagnostic probe is being pushed through the vessel.*

*88. The method of claim 74, wherein the intravascular image element is a cross-sectional intravascular ultrasound (IVUS) image.*

*89. The method of claim 74, wherein the intravascular image element is a graph representing the intravascular data.*

*90. The method of claim 89, wherein the graph represents at least one of blood pressure, blood flow velocity, shear stress, and fractional flow reserve.*

*91. A system for acquisition and co-registered display of intravascular information, comprising:*

*a flexible elongate member having a proximal end and a distal end;*

*a diagnostic probe located near the distal end of the flexible elongate member, and configured to obtain information related to a vessel;*

*a radiopaque marker located near the diagnostic probe;*

*a first memory portion for storing angiogram image data;*

*a second memory portion for storing intravascular data derived from information obtained by the diagnostic probe;*

*a third memory portion for storing radiopaque marker image data, the radiopaque marker image data being derived from information obtained from a fluoroscopic imaging device;*

*a display processor that combines data retrieved from the first memory portion, the second memory portion and the third memory portion to render a composite image including:*

*an enhanced radiological image derived from the angiogram image data comprising a superimposition of at least a portion of the angiogram data and the radiopaque marker image data and providing a location of the radiopaque marker based upon an actual location during active fluoroscopy and an estimated location during inactive fluoroscopy, wherein an error function is calculated based on a difference between the estimated location of the radiopaque marker and the actual location of the radiopaque marker when active fluoroscopy is resumed after inactive fluoroscopy and wherein the*

*error function is utilized to correct the estimated location of the radiopaque marker for the preceding period of inactive fluoroscopy,*

*an intravascular image element corresponding to the intravascular data, wherein the enhanced radiological image and the intravascular image element are displayed proximate each other; and*

*a cursor, displayed upon the enhanced radiological image, indicative of a location of the diagnostic probe while acquiring data for the intravascular image element presently displayed on the composite image, said cursor having a position that is based at least in part on third data derived from the radiopaque marker image data stored in the third memory portion.*

*92. The system of claim 91, wherein the estimated location of the radiopaque marker is calculated using a first multiplication coefficient if the diagnostic probe is being pulled through the vessel and a second multiplication coefficient if the diagnostic probe is being pushed through the vessel.*

*93. The system of claim 91, wherein the diagnostic probe is a catheter.*

*94. The system of claim 91, wherein the diagnostic probe is a guidewire.*

*95. The system of claim 91, wherein the diagnostic probe includes an ultrasound transducer.*

*96. The system of claim 91, wherein the diagnostic probe includes a pressure sensor.*

*97. The system of claim 91, wherein the intravascular image element is a cross-sectional intravascular ultrasound (IVUS) image.*

*98. The system of claim 91, wherein the intravascular image element is a graph representing the intravascular data.*

*99. The system of claim 98, wherein the graph represents at least one of blood pressure, blood flow velocity, shear stress, and fractional flow reserve.*

* * * * *